US012589228B2

(12) United States Patent
Sathyanarayanan

(10) Patent No.: US 12,589,228 B2
(45) Date of Patent: Mar. 31, 2026

(54) ACCESS SYSTEMS, DEVICES, AND METHODS THEREOF

(71) Applicant: Bard Access Systems, Inc., Salt Lake City, UT (US)

(72) Inventor: Gokulrangarajan Sathyanarayanan, Coimbatore (IN)

(73) Assignee: Bard Access Systems, Inc., Salt Lake City, UT (US)

( * ) Notice: Subject to any disclaimer, the term of this patent is extended or adjusted under 35 U.S.C. 154(b) by 937 days.

(21) Appl. No.: 17/720,050

(22) Filed: Apr. 13, 2022

(65) Prior Publication Data

US 2022/0323724 A1      Oct. 13, 2022

Related U.S. Application Data

(60) Provisional application No. 63/174,202, filed on Apr. 13, 2021.

(51) Int. Cl.
| | |
|---|---|
| *A61M 25/09* | (2006.01) |
| *A61M 25/00* | (2006.01) |
| *A61M 25/06* | (2006.01) |
| *A61M 29/02* | (2006.01) |

(52) U.S. Cl.
CPC .... *A61M 25/09041* (2013.01); *A61M 25/003* (2013.01); *A61M 25/065* (2013.01); *A61M 29/02* (2013.01); *A61M 2025/0031* (2013.01); *A61M 2025/09125* (2013.01)

(58) Field of Classification Search
CPC .......... A61M 25/09041; A61M 25/003; A61M 25/065; A61M 29/02; A61M 2025/0031; A61M 2025/09125; A61M 25/0113;
A61M 29/00; A61M 25/0606; A61M 25/01; A61M 25/0612; A61M 25/011; A61M 1/3661; A61B 17/3415; A61B 17/3439
See application file for complete search history.

(56) References Cited

U.S. PATENT DOCUMENTS

| | | | |
|---|---|---|---|
| 10,232,146 B2 | 3/2019 | Braithwaite et al. | |
| 2012/0059325 A1 | 3/2012 | Cluff et al. | |
| 2016/0067453 A1* | 3/2016 | Braithwaite | A61M 25/0631 604/164.08 |
| 2018/0311473 A1* | 11/2018 | Laby | A61M 25/0147 |
| 2021/0085927 A1 | 3/2021 | Howell | |

OTHER PUBLICATIONS

PCT/US2022/024666 filed Apr. 13, 2022 International Search Report and Written Opinion dated Aug. 25, 2022.

* cited by examiner

*Primary Examiner* — Laura A Bouchelle
*Assistant Examiner* — Sarah Dympna Grasmeder
(74) *Attorney, Agent, or Firm* — Rutan & Tucker LLP

(57) ABSTRACT

Disclosed are access systems, devices, and methods for internal access to a patient's body. For example, an access device for placing an acute dialysis catheter can include a frame; a housing, a pair of guidewire clamps, and a needle disposed on the frame; a dilator coupled to the frame, and an access guidewire in a ready-to-deploy state of the access device. The pair of guidewire clamps can be disposed on the frame between an end portion of the frame and a distal end of the housing for clamping the access guidewire. A needle hub of the needle can be disposed on the frame between the pair of guidewire clamps. The dilator can distally extend from the end portion of frame. A needle shaft of the needle can distally extend beyond a distal end of the dilator allowing the needle to establish an insertion site for the acute dialysis catheter.

19 Claims, 26 Drawing Sheets

*insertion site*

ACCESS SYSTEMS, DEVICES, AND METHODS THEREOF

PRIORITY

This application claims the benefit of priority to U.S. Provisional Patent Application No. 63/174,202, filed Apr. 13, 2021, which is incorporated by reference in its entirety into this application.

BACKGROUND

Acute dialysis catheters are indicated for attaining short-term intravascular access by way of the jugular, subclavian, or femoral vein for hemodialysis, hemoperfusion, or apheresis therapy. Such acute dialysis catheters are placed in patients manually. For example, an acute dialysis catheter can be placed in a patient in accordance with a procedure including at least the following steps: 1) inserting a needle into a vein of the patient, thereby creating an insertion site; 2) advancing an access guidewire into the vein by way of the needle; 3) removing the needle; 4) dilating the insertion site with a dilator over the access guidewire; 5) inserting the acute dialysis catheter over the access guidewire; and 5) removing the access guidewire.

Problems with placing an acute dialysis catheter in accordance with the foregoing include 1) needle-hub cracking or other breakage when creating the insertion site; 2) prolonged procedure time due a substantial number of steps and idle time between those steps; and 3) a substantial number of different components for which sterility must be maintained during the procedure for placing the acute dialysis catheter. In view of the foregoing, access systems, devices, and methods thereof are needed to address the foregoing problems with placing at least acute dialysis catheters.

Disclosed herein are access systems, devices, and methods for placing at least acute dialysis catheters.

SUMMARY

Disclosed herein is an access device for internal access to a body of a patient. The access device includes, in some embodiments, a longitudinal frame; a longitudinal housing, a pair of guidewire clamps, and a needle disposed on the frame; and a dilator coupled to the frame. The frame includes a distal end portion. The pair of guidewire clamps is disposed on the frame between the end portion of the frame and a distal end of the housing in a ready-to-deploy state of the access device. Each guidewire clamp of the pair of guidewire clamps is configured to clamp an access guidewire disposed in the access device. The needle includes a needle shaft coupled to a needle hub. The needle hub is disposed on the frame between the pair of guidewire clamps. The dilator distally extends from the end portion of frame in the ready-to-deploy state of the access device. The needle shaft distally extends beyond a distal end of the dilator in the ready-to-deploy state of the access device such that the needle is allowed to establish an insertion site for the internal access to the body of the patient.

In some embodiments, the frame includes a plurality of rails proximally extending from the end portion of the frame. The housing includes a pair of housing channels configured to slidably accept therein a first pair of rails of the plurality of rails. The needle hub includes at least a pair of needle-hub peripheral through holes configured to slidably accept therein a second pair of rails of the plurality of rails.

In some embodiments, at least one guidewire clamp of the pair of guidewire clamps includes a pair of guidewire-clamp peripheral through holes. The pair of guidewire-clamp peripheral through holes is configured to slidably accept therein the second pair of rails.

In some embodiments, the needle hub and at least one guidewire clamp of the pair of guidewire clamps includes a pair of cutouts. The pair of cutouts is configured to bypass the first pair of rails.

In some embodiments, the first pair of rails and the second pair of rails are orthogonal to each other.

In some embodiments, the first pair of rails is longer than the second pair of rails. The first pair of rails being longer than the second pair of rails allows the housing to slide beyond a proximal end of the second pair of rails for removal of at least the needle from the access device.

In some embodiments, the housing is configured to accept therein a catheter tube. The housing is configured to maintain sterility of the catheter tube during a procedure for placing the catheter tube in the body of the patient with the access device after dilation of the insertion site with the dilator.

In some embodiments, the housing is transparent. The housing being transparent allows the catheter tube to be viewed while distally advancing the housing over the frame and simultaneously threading the catheter tube over a proximal end of the access guidewire.

In some embodiments, the housing includes a sidewall guidewire clamp disposed in a sidewall of the housing. The sidewall guidewire clamp is configured to clamp and hold the access guidewire in position in the needle shaft while establishing the insertion site with the needle. The sidewall guidewire clamp is also configured to open and allow the access guidewire to be distally advanced into the body of the patient through the insertion site.

In some embodiments, each guidewire clamp of the pair of guidewire clamps includes a captive but movable slide. The moveable slide is configured to slide into a groove of the guidewire clamp and clamp the access guidewire when the access guidewire is threaded through a central through hole in the guidewire clamp.

In some embodiments, each guidewire clamp of the pair of guidewire clamps includes a stationary slide disposed in the groove of the guidewire clamp on an opposite side of the central through hole from the moveable slide. The stationary slide is configured to oppose the movable slide when clamping the access guidewire.

In some embodiments, the pair of guidewire clamps includes a proximal guidewire clamp and a distal guidewire clamp.

In some embodiments, the distal guidewire clamp proximally extends from the end portion of frame to which the distal guidewire clamp is coupled in the ready-to-deploy state of the access device.

In some embodiments, the frame, the housing, the dilator, and the distal guidewire clamp are configured to split along their lengths for removal from around at least the access guidewire when the access guidewire is disposed in the body of the patient through the insertion site.

In some embodiments, the access device further includes a plurality of fasteners. The plurality of fasteners is configured to fasten components of the access device together as well as keep the components in position in the ready-to-deploy state of the access device. The components include at least the housing, at least one guidewire clamp of the pair of guidewire clamps, the needle hub, and the dilator.

In some embodiments, each fastener of the plurality of fasteners is irremovably coupled by a hinge to a hinged-side fastener rail. Each fastener of the plurality of fasteners is removably fastened to a fastening-side fastener rail in the ready-to-deploy state of the access device.

In some embodiments, at least one fastener of the plurality of fasteners is configured to double for fastening the housing and at least one guidewire clamp of the pair of guidewire clamps. The at-least-one fastener is configured to fasten the housing in the ready-to-deploy state of the access device. The at-least-one fastener is also configured to fasten at least one guidewire clamp of the pair of guidewire clamps for clamping the access guidewire while proximally withdrawing the needle from the insertion site.

Also disclosed herein is an access system for internal access to a body of a patient. The access system includes, in some embodiments, a catheter and an access device. The access device includes a longitudinal frame; a longitudinal housing, a pair of guidewire clamps, and a needle disposed on the frame; and a dilator coupled to the frame. The frame includes a distal end portion. The housing is disposed on the frame, and a catheter tube of the catheter is disposed in the housing a ready-to-deploy state of the access system. The pair of guidewire clamps is disposed on the frame between the end portion of the frame and a distal end of the housing in a ready-to-deploy state of the access system. Each guidewire clamp of the pair of guidewire clamps is configured to clamp an access guidewire disposed in the access device. The needle includes a needle shaft coupled to a needle hub. The needle hub is disposed on the frame between the pair of guidewire clamps. The dilator distally extends from the end portion of frame in the ready-to-deploy state of the access system. The needle shaft distally extends beyond a distal end of the dilator in the ready-to-deploy state of the access system such that the needle is allowed to establish an insertion site for the internal access to the body of the patient.

In some embodiments, the catheter is an acute dialysis catheter. The internal access to the body of the patient is vascular access by way of a jugular, a subclavian, or a femoral vein of the patient.

Also disclosed herein is a method of an access device for internally accessing a body of a patient. The method includes, in some embodiments, an insertion site-establishing step, an access guidewire-advancing step, a needle-withdrawing step, a dilating step, a component-removing step, and a catheter-inserting step. The insertion site-establishing step includes establishing an insertion site with a needle of the access device. The needle includes a needle shaft coupled to a needle hub. The needle hub is disposed on a frame of the access device between a pair of guidewire clamps. The access guidewire-advancing step includes distally advancing an access guidewire through the needle and into the body of the patient. The access guidewire-advancing step is performed by feeding the access guidewire through an open sidewall guidewire clamp disposed in a sidewall of a housing of the access device. The needle-withdrawing step includes proximally withdrawing the needle from both the patient and the access device. With respect to withdrawing the needle from the access device, the needle-withdrawing step includes withdrawing the needle hub beyond a proximal end of a second pair of rails of a plurality of rails of the frame. The dilating step includes dilating the insertion site with a dilator over the access guidewire. The dilator distally extends from an end portion of the frame to which the dilator is coupled. The component-removing step includes removing any remaining components of the access device from around the access guidewire. The component-removing step is performed by separating top and bottom portions of the remaining components of the access device and withdrawing them from the access guidewire. The catheter-inserting step includes inserting a catheter tube of a catheter into the patient over the access guidewire.

These and other features of the concepts provided herein will become more apparent to those of skill in the art in view of the accompanying drawings and following description, which describe particular embodiments of such concepts in greater detail.

DRAWINGS

DESCRIPTION

Figure 1:
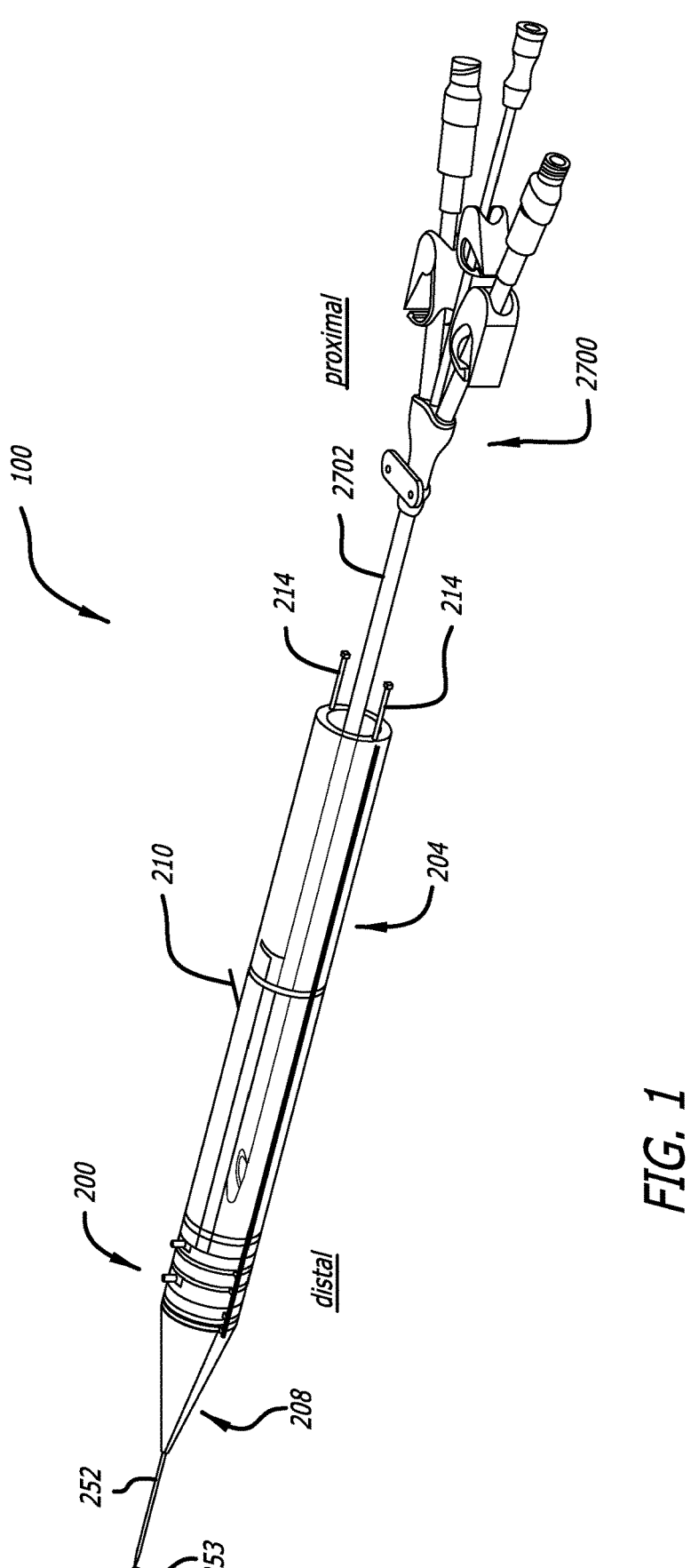
FIG. 1 illustrates an access system including a catheter and an access device in a ready-to-deploy state thereof in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, problems with placing an acute dialysis catheter include 1) needle-hub cracking or other breakage when creating an insertion site; 2) prolonged procedure time due a substantial number of steps and idle time between those steps; and 3) a substantial number of different components for which sterility must be maintained during a procedure for placing the acute dialysis catheter. In view of the foregoing, access systems, devices, and methods thereof are needed to address the foregoing problems with placing at least acute dialysis catheters. As such access systems, devices, and methods for placing at least acute dialysis catheters are disclosed.

It should be understood that while access systems, devices, and methods set forth herein are primarily described in terms of establishing intravascular access with acute dialysis catheters, the access systems, devices, and methods set forth herein are not limited thereto. Indeed, the access systems, devices, and methods set forth herein can be adapted for establishing intravascular access with other catheters (e.g., peripherally inserted central catheters ["PICCs"], central venous catheters ["CVCs"], or the like) or even more general internal access with other medical devices.

Access Systems

FIG. 1 illustrates an access system 100 in accordance with some embodiments.

As shown, the access system 100 includes a catheter 2700 and an access device 200 in a ready-to-deploy state of the access system 100. The access system 100 including the access device 200 and the catheter 2700 is configured for internal access to a body of a patient.

The catheter 2700 is an acute dialysis catheter, and the internal access to the body of the patient for which the catheter 2700 is configured is vascular access by way of a jugular, a subclavian, or a femoral vein of the patient. As set forth above, the access system 100 can be adapted for other catheters or medical devices. Of course, if the access system 100 is adapted for the other catheters or medical devices, the internal access to the body of the patient will differ in accordance with the other catheters or medical devices.

The access device 200 is set forth in detail in the following section.

Access Devices

Figure 2:
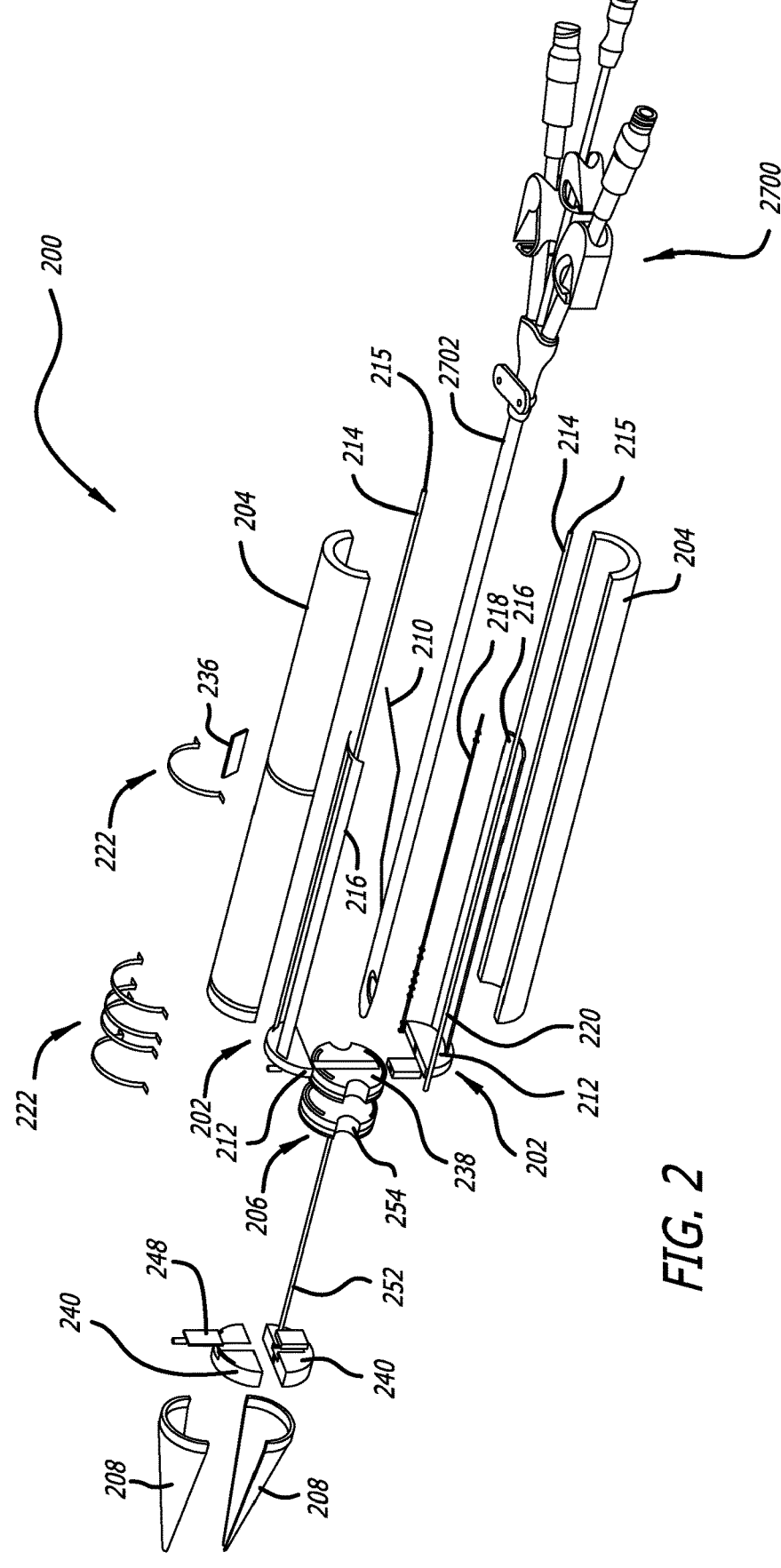
FIG. 2 illustrates an exploded view of the access device in accordance with some embodiments.

Whereas FIG. 1 illustrates the access system 100 and the access device 200 thereof in the ready-to-deploy state, FIG. 2 illustrates an exploded view of the access device 200 in accordance with some embodiments. FIGS. 3-26 illustrate the access device 200 in various operating states thereof. As needed, figures of FIGS. 3-26 are further referenced immediately below and in the following section in accordance with description for the various operating states of the access device 200 as well as steps for using the access device 200.

As shown, the access device 200 includes a longitudinal frame 202, a longitudinal housing 204, a pair of guidewire clamps (i.e., the proximal guidewire clamp 238 and the distal guidewire clamp 240), a needle 206, a dilator 208, and an access guidewire 210. In the ready-to-deploy state of the access device 200, the housing 204 is disposed on the frame 202, the pair of guidewire clamps is disposed on the frame 202, the needle 206 is disposed on the frame 202, and the dilator 208 is coupled to the frame 202. Further in the ready-to-deploy state of the access device 200, the needle 206 or, more particularly, the needle shaft 252 of the needle 206, distally extends beyond a distal end of the dilator 208 such that the needle 206 is allowed to establish an insertion site for internal access to a body of a patient.

The frame 202 includes a distal end portion 212 (e.g., a disk or annulus) and a plurality of rails (e.g., the first pair of rails 214 and the second pair of rails 216) proximally extending from the end portion 212 of the frame 202. Notably, the frame 202 including the end portion 212 thereof is configured to split along its length for removal from around at least the access guidewire 210 when the access guidewire 210 is disposed in a body of a patient through an insertion site.

The plurality of rails includes a first pair of rails 214 and a second pair rails 216 that are orthogonal to each other. The first pair of rails 214 is longer than the second pair of rails 216. The first pair of rails 214 being longer than the second pair of rails 216 allows the housing 204 to slide beyond a proximal end of the second pair of rails 216 for removal of at least the needle 206 and the proximal guidewire clamp 238 from the access device 200. Indeed, as set forth below, both the needle 206 and the proximal guidewire clamp 238 are allowed to slide beyond the proximal end of the second pair of rails 216 for removal from the access device 200 while the housing 204 is beyond the proximal end of the second pair of rails 216.

The first pair of rails 214 includes side rails upon which the housing 204 is slidably and, optionally, captively disposed. The first pair of rails 214 can be a pair of rods that are round, square, rectangular, hexagonal, or the like in cross section. When configured to keep the housing 204 captively disposed on the first pair of rails 214, each rail of the first pair of rails can include a stop 215 at a proximal end thereof.

As set forth below, the stop 215 is configured to stop a distal portion of the housing 204 from disengaging from the first pair of rails 214 when the housing 204 is proximally withdrawn from the end portion 212 of the frame 202.

The second pair of rails 216 includes top and bottom rails upon which the housing 204 is slidably disposed in the ready-to-deploy state of the access device 200. The second pair of rails 216 can be a pair of flat or arcuate bars. In certain operating states of the access device 200, the housing 204 is removed from the second pair of rails 216 such as for removal of both the needle 206 and the proximal guidewire clamp 238 from the access device 200. For this reason, the second pair of rails 216 lacks a stop such as the stop 215 at the proximal end of each rail of the first pair of rails 214.

The plurality of rails further includes a pair of fastener rails proximally extending from the end portion 212 of the frame 202. The pair of fastener rails includes a hinged-side fastener rail 218 and fastening-side fastener rail 220 outboard of the first pair of rails 214. The plurality of fasteners 222 set forth below is irremovably coupled by hinges to the hinged-side fastener rail 218 and removably fastened to the fastening-side fastener rail 220 in at least the ready-to-deploy state of the access device 200.

Figure 6:
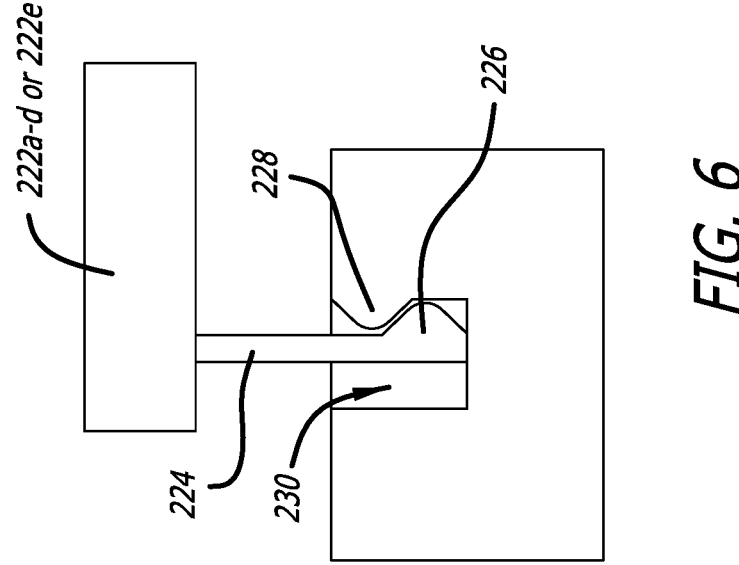
FIG. 6 illustrates a cross-sectional view of a fastener of the plurality of fasteners fastened to the fastening-side fastener rail in accordance with some embodiments.
Figure 5:
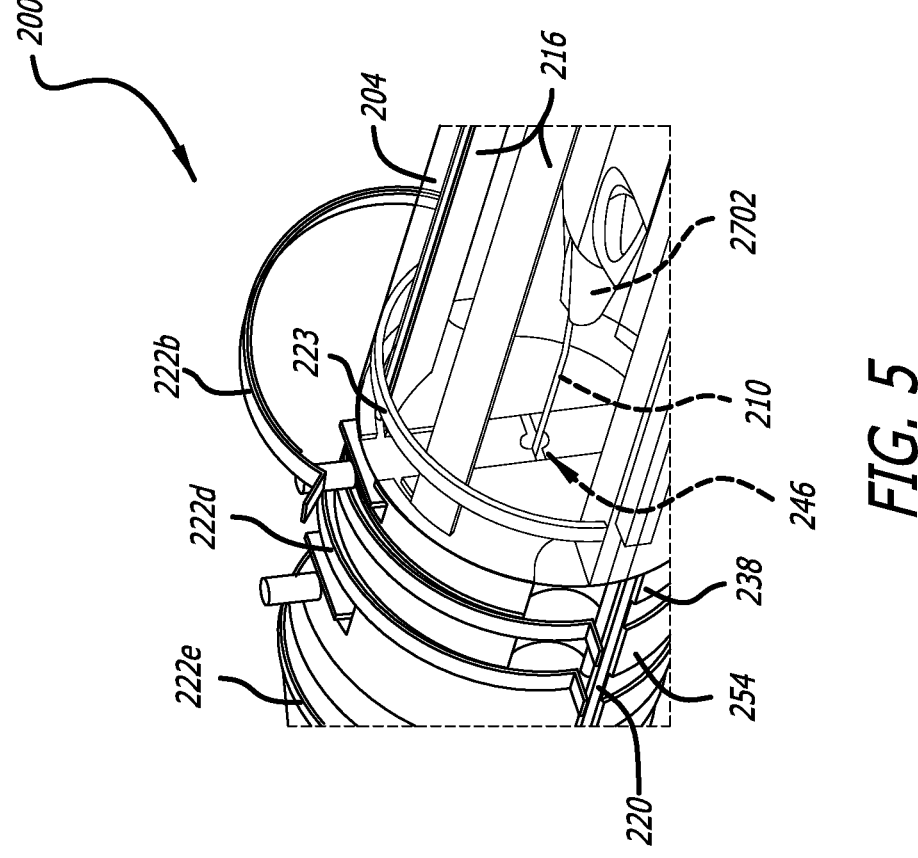
FIG. 5 illustrates a fastener of the plurality of fasteners unfastened from a fastening-side fastener rail of the pair of fastener rails in accordance with some embodiments.

As shown, the access device 200 further includes a plurality of fasteners 222 including at least fastener 222*a*, fastener 222*b*, fastener 222*c*, fastener 222*d*, and fastener 222*e*, wherein fasteners 222*a* and 222*e* are respectively the most proximal and distal fasteners of the plurality of fasteners 222 of the access device 200. Each fastener of the plurality of fasteners 222 is irremovably coupled by a hinge to the hinged-side fastener rail 218. In addition, each fastener of the plurality of fasteners 222 is removably fastened to the fastening-side fastener rail 220 in at least the ready-to-deploy state of the access device 200. Indeed, as shown in FIGS. 5 and 6, each fastener of the plurality of fasteners 222 incudes a tab 224 including an interlocking feature 226 configured to interlock with a complementary interlocking feature 228 in a receptacle 230 of a plurality of receptacles in the fastening-side fastener rail 220.

The plurality of fasteners 222 is configured to fasten components of the access device 200 together and keep the components in position in the ready-to-deploy state of the access device 200 as well as various operating states of the access device 200. Such components include at least the housing 204, at least one guidewire clamp (e.g., the proximal guidewire clamp 238) of the pair of guidewire clamps, the needle 206 or, more particularly, the needle hub 254 of the needle 206, and the dilator 208, and each component of such components includes a complementary groove 223 configured to receive a body of a fastener of the plurality of fasteners 222. At least one fastener (e.g., the fastener 222*a*) of the plurality of fasteners 222 is configured to double for fastening the housing 204 and at least one guidewire clamp (e.g., the proximal guidewire clamp 238 or the distal guidewire clamp 240) of the pair of guidewire clamps. The at-least-one fastener is configured to fasten the housing 204 in the ready-to-deploy state of the access device 200. The at-least-one fastener is also configured to fasten at least one guidewire clamp (e.g., the proximal guidewire clamp 238) of the pair of guidewire clamps for clamping the access guidewire 210 while proximally withdrawing the needle 206 or, more specifically, the needle shaft 252 from an insertion site in a body of a patient.

Figure 13:
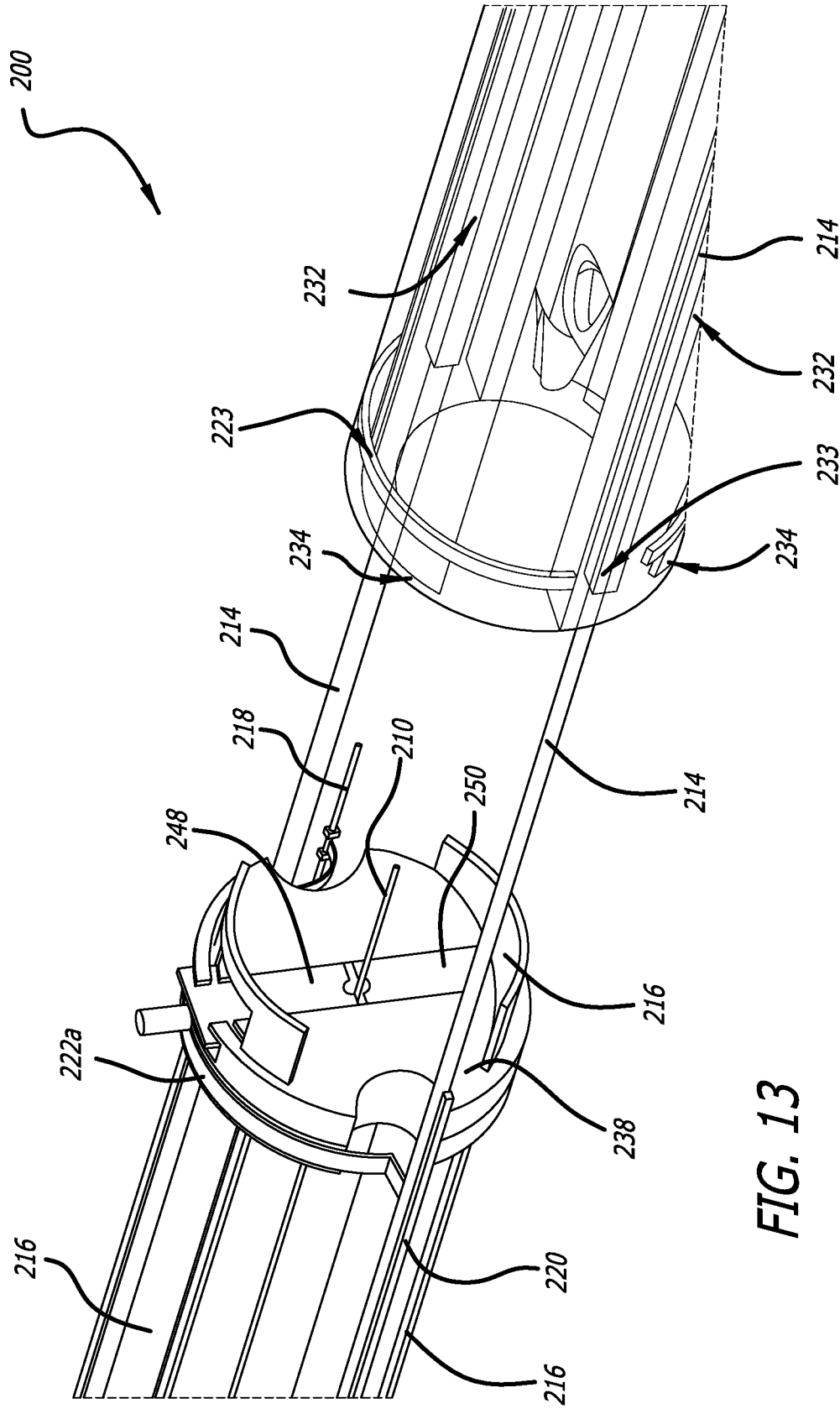
FIG. 13 illustrates the first fastener fastened over the proximal guidewire clamp and an access guidewire clamped by the proximal guidewire clamp in accordance with some embodiments.

As best shown in FIG. 13, the housing includes a first pair of housing channels 232 configured to slidably accept therein the first pair of rails 214 of the plurality of rails as well as a second pair of housing channels 234 configured to slidably accept therein the second pair of rails 216 of the plurality of rails. Each housing channel of the first pair of housing channels 232 can include a constriction 233 in a distal portion of the housing channel. The constriction 233 is configured to prevent the stop 215 from passing there-through, thereby stopping the distal portion of the housing 204 from disengaging from the first pair of rails 214 when the housing 204 is proximally withdrawn from the end portion 212 of the frame 202. The second pair of housing channels 234 lacks such a constriction as removal of at least the needle 206 and the proximal guidewire clamp 238 from the access device 200 is made possible by sliding the housing 204 beyond the proximal end of the second pair of rails 216.

The housing 204 is configured to accept therein a catheter tube 2702 of the catheter 2700 during a procedure for placing the catheter tube 2702 in a body of a patient with the access device 200. Being that the catheter tube 2702 is disposed in the housing 204 during the procedure, the housing 204 maintains sterility of the catheter tube 2702 during the procedure. Advantageously, the housing 204 is transparent as well. The housing 204 being transparent allows the catheter tube 2702 to be viewed while distally advancing the housing 204 over the frame 202 and simultaneously threading the catheter tube 2702 over a proximal end of the access guidewire 210 for subsequently advancing the catheter over the access guidewire 210 into the body of the patient by way of an insertion site. Notably, the housing 204 is configured to split along its length for removal from around at least the access guidewire 210 when the access guidewire 210 is disposed in the body of the patient through the insertion site.

The housing 204 further includes a sidewall guidewire clamp 236 disposed in a sidewall of the housing 204, thereby forming a portion of the sidewall of the housing 204 when the sidewall guidewire clamp 236 is closed. The sidewall guidewire clamp 236 is configured to clamp and hold the access guidewire 210 in position in the needle shaft 252 while establishing an insertion site in a body of a patient with the needle 206. The sidewall guidewire clamp 236 is also configured to open and allow the access guidewire 210 to be distally advanced into the body of the patient through the insertion site.

As shown, the pair of guidewire clamps includes a proximal guidewire clamp 238 and a distal guidewire clamp 240. The pair of guidewire clamps is disposed on the frame 202 between the end portion 212 of the frame 202 and a distal end of the housing 204 in the ready-to-deploy state of the access device 200. Indeed, the distal guidewire clamp 240 proximally extends from the end portion 212 of frame 202 to which the distal guidewire clamp is coupled or at least abuts in the ready-to-deploy state of the access device, and the proximal guidewire clamp 238 abuts the distal end of the housing 204 in the ready-to-deploy state of the access device 200.

Figures 9, 10:
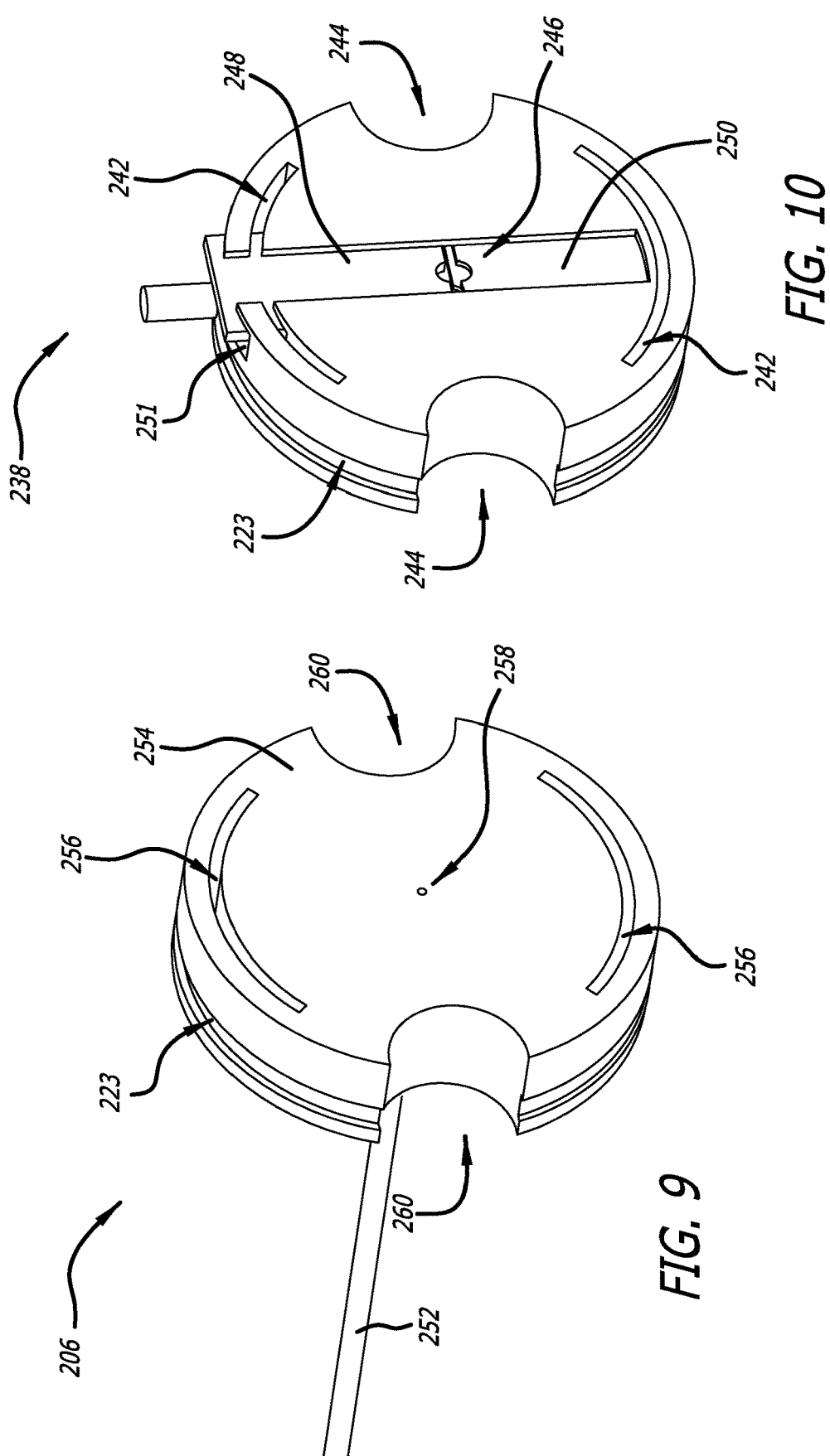
FIG. 9 illustrates a needle hub of a needle in accordance with some embodiments.
FIG. 10 illustrates a proximal guidewire clamp in accordance with some embodiments.
Figure 11:
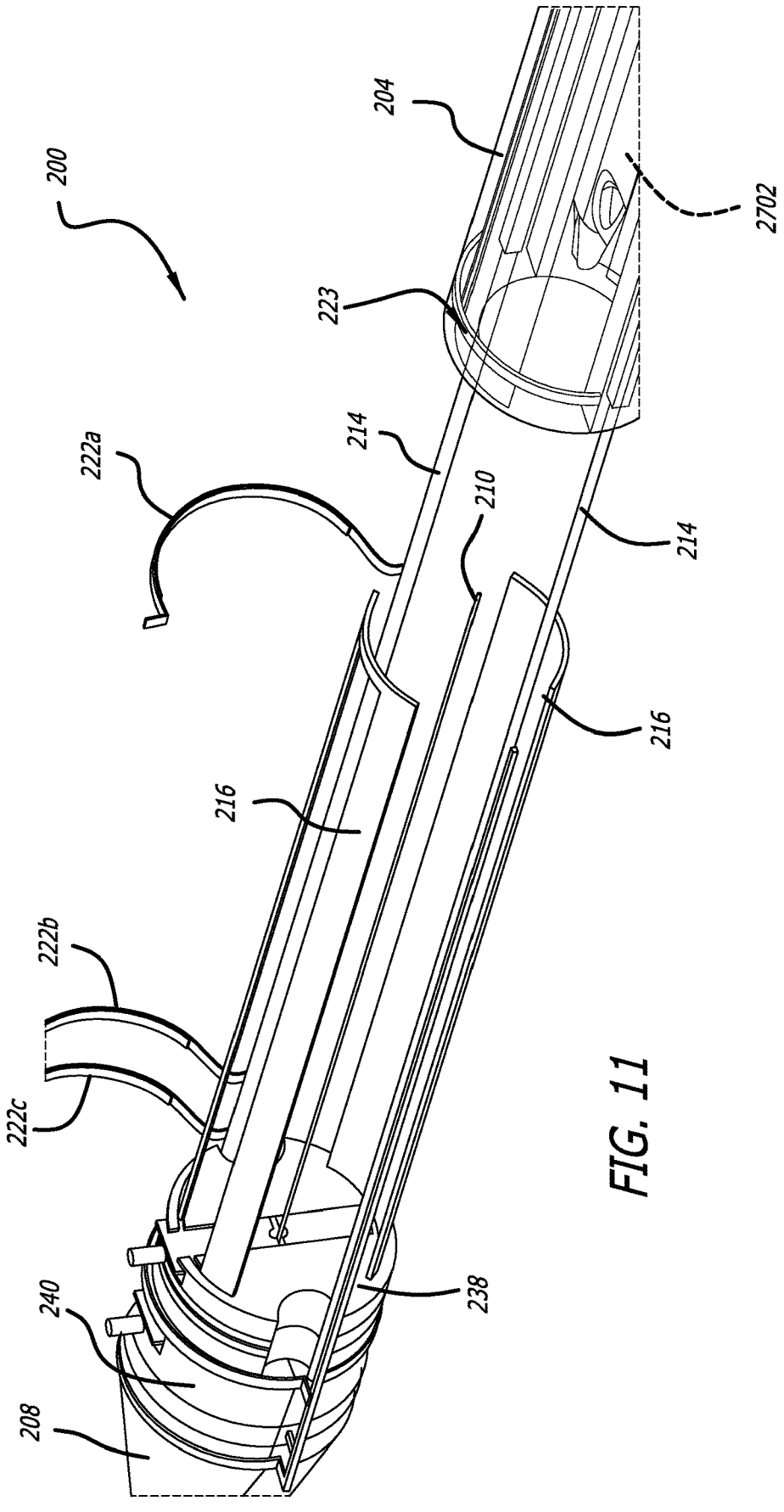
FIG. 11 illustrates a third fastener of the plurality of fasteners over the proximal guidewire clamp but unfastened from the fastening-side fastener rail in accordance with some embodiments.
Figure 12:
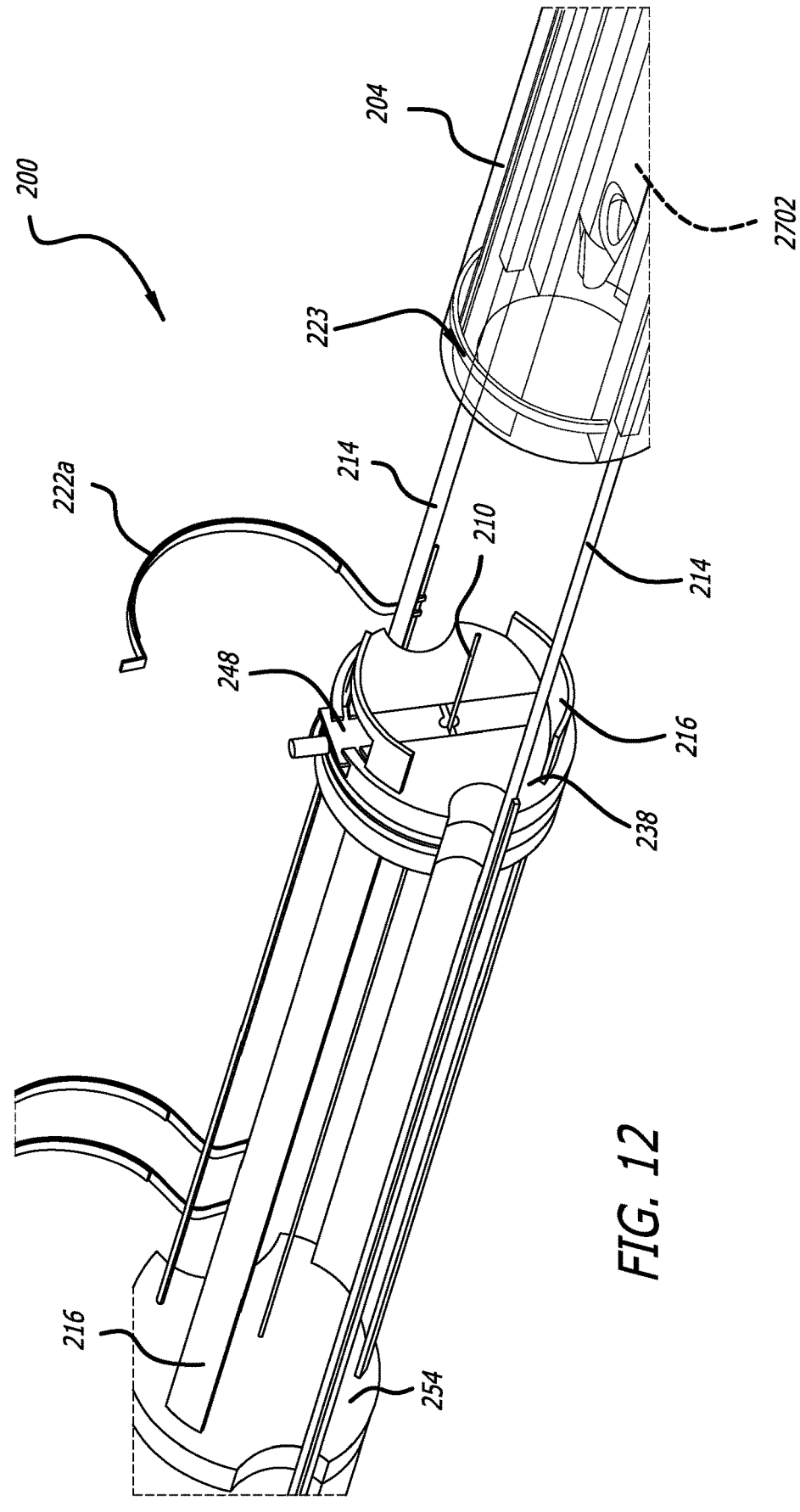
FIG. 12 illustrates the proximal guidewire clamp proximally withdrawn to the first fastener in accordance with some embodiments.

As best shown in FIG. 10, at least one guidewire clamp of the pair of guidewire clamps includes a pair of peripheral through holes 242; however, in the embodiment of the access device 200 shown and described herein, each guidewire clamp of the proximal guidewire clamp 238 and the distal guidewire clamp 240 includes the pair of peripheral through holes 242 therethrough. The pair of peripheral through holes 242 is configured to slidably accept therein the second pair of rails 216. Thus, the pair of peripheral through holes 242 includes top and bottom through holes respectively for the top and bottom rails of the second pair of rails 216. Because the second pair of rails 216 can be a pair of flat or arcuate bars, the pair of peripheral through holes 242 can respectively be a pair of flat or arcuate through holes.

As further shown in FIG. 10, at least one guidewire clamp of the pair of guidewire clamps includes a pair of cutouts 244; however, in the embodiment of the access device 200 shown and described herein, only the proximal guidewire clamp 238 includes the pair of cutouts 244. The pair of cutouts 244 is configured to bypass the longer first pair of rails 214 such that the proximal guidewire clamp 238 is removable from the access device 200 when slid beyond the proximal end of the shorter second pair of rails 216. Thus, the pair of cutouts 244 includes side cutouts respectively for the side rails of the first pair of rails 214. Because the pair of cutouts 244 is configured to bypass the longer first pair of rails 214, the pair of cutouts 244 need not match that of the first pair of rails 214, which, as set forth above, can be a pair of rods that are round, square, rectangular, hexagonal, or the like in cross section.

The pair of guidewire clamps is configured to clamp the access guidewire 210 in the ready-to-deploy state of the access device 200 as well as various operating states of the access device 200. Because each guidewire clamp of the pair of guidewire clamps is configured to clamp the access guidewire 210 independent of the other, each guidewire clamp includes a central through hole 246, a captive but movable slide 248, and a stationary slide 250 opposite the movable slide 248 across the central through hole 246 to clamp the access guidewire 210. (See FIG. 10.) The movable slide 248 is configured to slide into a groove 251 of the proximal guidewire clamp 238 or the distal guidewire clamp 240 and clamp the access guidewire 210 after the access guidewire 210 is threaded through the central through hole 246 in the guidewire clamp. The stationary slide 250, which is also in the groove 251 across the central through hole 246, is configured to oppose the movable slide 248 when clamping the access guidewire 210.

Notably, at least the distal guidewire clamp 240 is configured to split in accordance with similarly configured components (e.g., the frame 202, the housing 204, and the dilator 208) for removal from around at least the access guidewire 210 when the access guidewire 210 is disposed in a body of a patient through an insertion site.

As shown, the needle 206 includes a needle shaft 252 coupled to a needle hub 254 with the needle hub 254 disposed on the frame 202 between the pair of guidewire clamps and the needle shaft 252 distally extending through the central through hole 246 of the distal guidewire clamp 240 in at least the ready-to-deploy state of the access device 200. The needle shaft 252 terminates in a needle tip 253 configured to percutaneously puncture a patient. Indeed, the needle shaft 252 and the needle tip 253 thereof distally extends beyond the distal end of the dilator 208 in the ready-to-deploy state of the access device 200 such that the needle 206 is allowed to percutaneously puncture the patient and establish an insertion site in a body of the patient.

As best shown in FIG. 10, the needle hub 254 includes a pair of peripheral through holes 256 and a central through hole 258 in line with a lumen of the needle shaft 252. The pair of peripheral through holes 256 is configured to slidably accept therein the second pair of rails 216. Thus, the pair of peripheral through holes 256 includes top and bottom through holes respectively for the top and bottom rails of the second pair of rails 216. Because the second pair of rails 216 can be a pair of flat or arcuate bars, the pair of peripheral through holes 256 can respectively be a pair of flat or arcuate through holes.

As further shown in FIG. 10, the needle hub 254 includes a pair of cutouts 260. The pair of cutouts 260 is configured to bypass the longer first pair of rails 214 such that the needle 206 is removable from the access device 200 when the needle hub 254 is slid beyond the proximal end of the shorter second pair of rails 216. Thus, the pair of cutouts 260 includes side cutouts respectively for the side rails of the first pair of rails 214. Because the pair of cutouts 260 is configured to bypass the longer first pair of rails 214, the pair of cutouts 260 need not match that of the first pair of rails 214, which, as set forth above, can be a pair of rods that are round, square, rectangular, hexagonal, or the like in cross section.

As shown, the dilator 208 distally extends from the end portion 212 of the frame 202 to which it is coupled in at least the ready-to-deploy state of the access device 200. The dilator 208 is configured with a suitable taper to dilate one or more tissues of an insertion site in a body of a patient over the access guidewire 210 subsequent to removal of the needle 206 from the access device 200. Notably, at least the dilator 208 is configured to split along its length for removal from around at least the access guidewire 210 when the access guidewire 210 is disposed in the body of the patient through the insertion site.

Methods

Methods include a method of using the access system 100 or the access device 200 thereof for internally accessing a body of a patient. Broadly, such a method can include an insertion site-establishing step, an access guidewire-advancing step, a needle-withdrawing step, a dilating step, a component-removing step, and a catheter-inserting step, each step of which is set forth, in turn, below with additional description.

The insertion site-establishing step includes establishing an insertion site with the needle 206 of the access device 200. As set forth above, the needle 206 includes the needle shaft 252 coupled to the needle hub 254, which is disposed on the frame 202 of the access device 200 between the pair of guidewire clamps (e.g., the proximal guidewire clamp 238 and the distal guidewire clamp 240).

The access guidewire-advancing step includes distally advancing the access guidewire 210 through the needle 206 and into the body of the patient. The access guidewire-advancing step is performed by feeding the access guidewire 210 through the sidewall guidewire clamp 236 disposed in the sidewall of the housing 204 of the access device 200 when the sidewall guidewire clamp 236 is open.

The needle-withdrawing step includes proximally withdrawing the needle 206 from both the patient and the access device 200. With respect to withdrawing the needle 206 from the access device 200, the needle-withdrawing step includes withdrawing the needle hub 254 beyond the proximal end of the second pair of rails 216 of the plurality of rails of the frame 202.

The dilating step includes dilating the insertion site with the dilator 208 over the access guidewire 210. The dilator 208 distally extends from the end portion 212 of the frame 202 to which the dilator 208 is coupled.

The component-removing step includes removing any remaining components of the access device 200 from around the access guidewire 210. The component-removing step is performed by separating top and bottom portions of the remaining components of the access device 200 and withdrawing them from the access guidewire 210. Such remain components include the frame 202, the housing 204, at least one guidewire clamp (e.g., the distal guidewire clamp 240) of the pair of guidewire clamps, and the dilator 208.

The catheter-inserting step includes inserting the catheter tube 2702 of the catheter 2700 into the patient over the access guidewire 210.

EXAMPLES

Following on the broadly described method of using the access system 100 or the access device 200 thereof, a more detailed step-by-step example of using the access system 100 or the access device 200 for internally accessing a body of a patient is set forth below to add further detail to the broadly described method set forth above. For convenience, each step of the step-by-step example is set forth below as a numbered step in its own paragraph; however, it should be understood the numbered steps do not supply a serial limitation as there can be a different number of steps than that set forth below. Indeed, some of the steps can, in turn, include one or more steps that intervene with a subsequently numbered step. In addition, unless context indicates otherwise, some of the steps can be performed in a different order than that presented.

Step 0: In the ready-to-deploy state of the access system 100 shown in FIG. 1, each fastener of the plurality of fasteners 222 is fastened, thereby fastening together all the components of the access device 200 in a single structural unit with the needle shaft 252 extending from the distal end of the dilator 208 for a percutaneous puncture of the patient.

Step 1: Percutaneously puncture a body of the patient with the needle 206 and establish an insertion site in the body of the patient.

Figure 3:
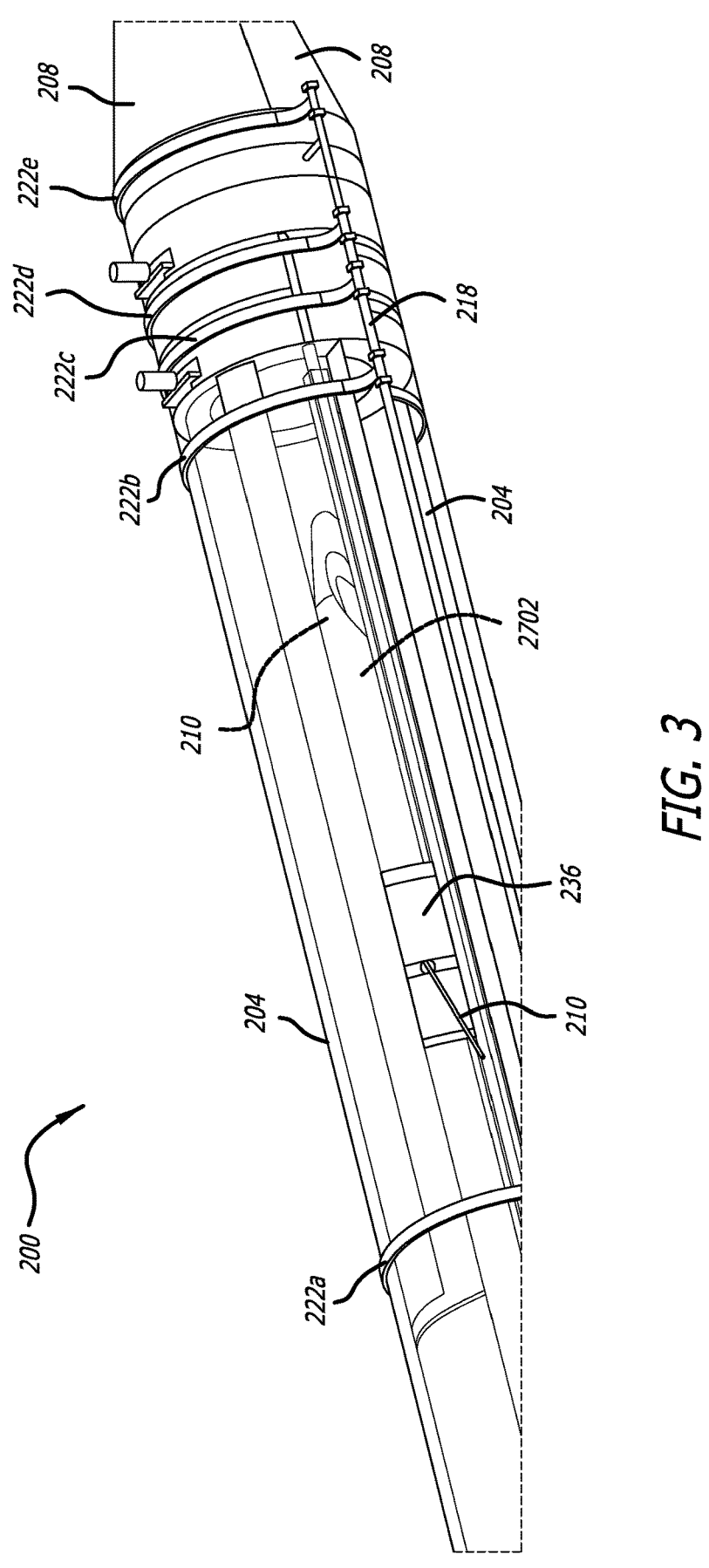
FIG. 3 illustrates a sidewall guidewire clamp disposed in a sidewall of a housing of the access device in accordance with some embodiments.
Figure 4:
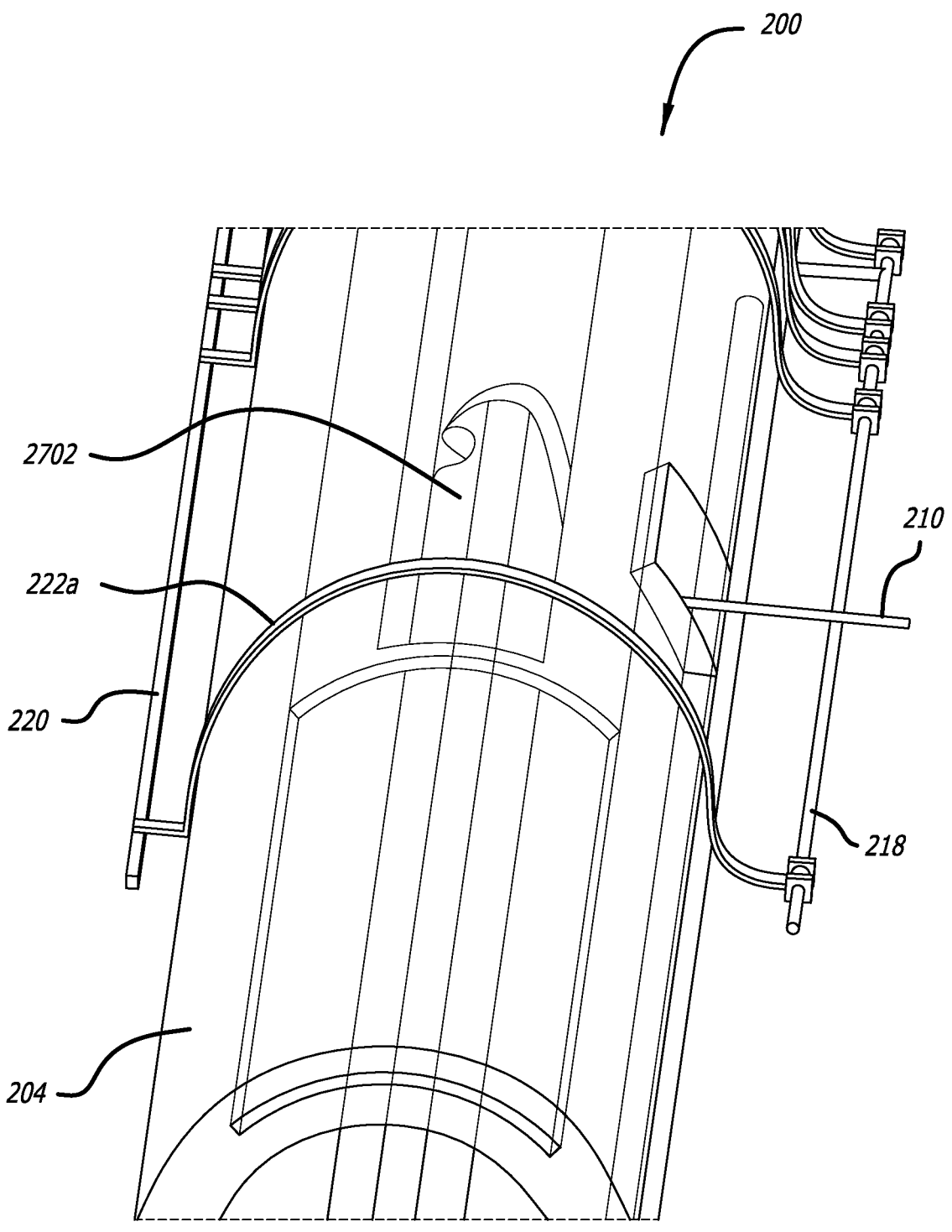
FIG. 4 illustrates a plurality of fasteners coupled to a pair of fastener rails of a frame in accordance with some embodiments.

Step 2: Open the sidewall guidewire clamp 236 disposed in the sidewall of the housing 204 of the access device 200 as shown in FIG. 3 to create an opening in the sidewall of the housing 204.

Step 3: As further shown in FIG. 3, advance the access guidewire 210 into the patient by feeding it through the opening created in the sidewall of the housing 204 by the opening of the sidewall guidewire clamp 236 as well as through the central through hole 246 of the proximal guidewire clamp 238, which can be open by default, the central through hole 258 of needle hub 254, and the lumen of the needle shaft 252. The needle shaft 252 passes through both the distal guidewire clamp 240 and the dilator 208 before extending past the distal end of the dilator 208.

Figure 7:
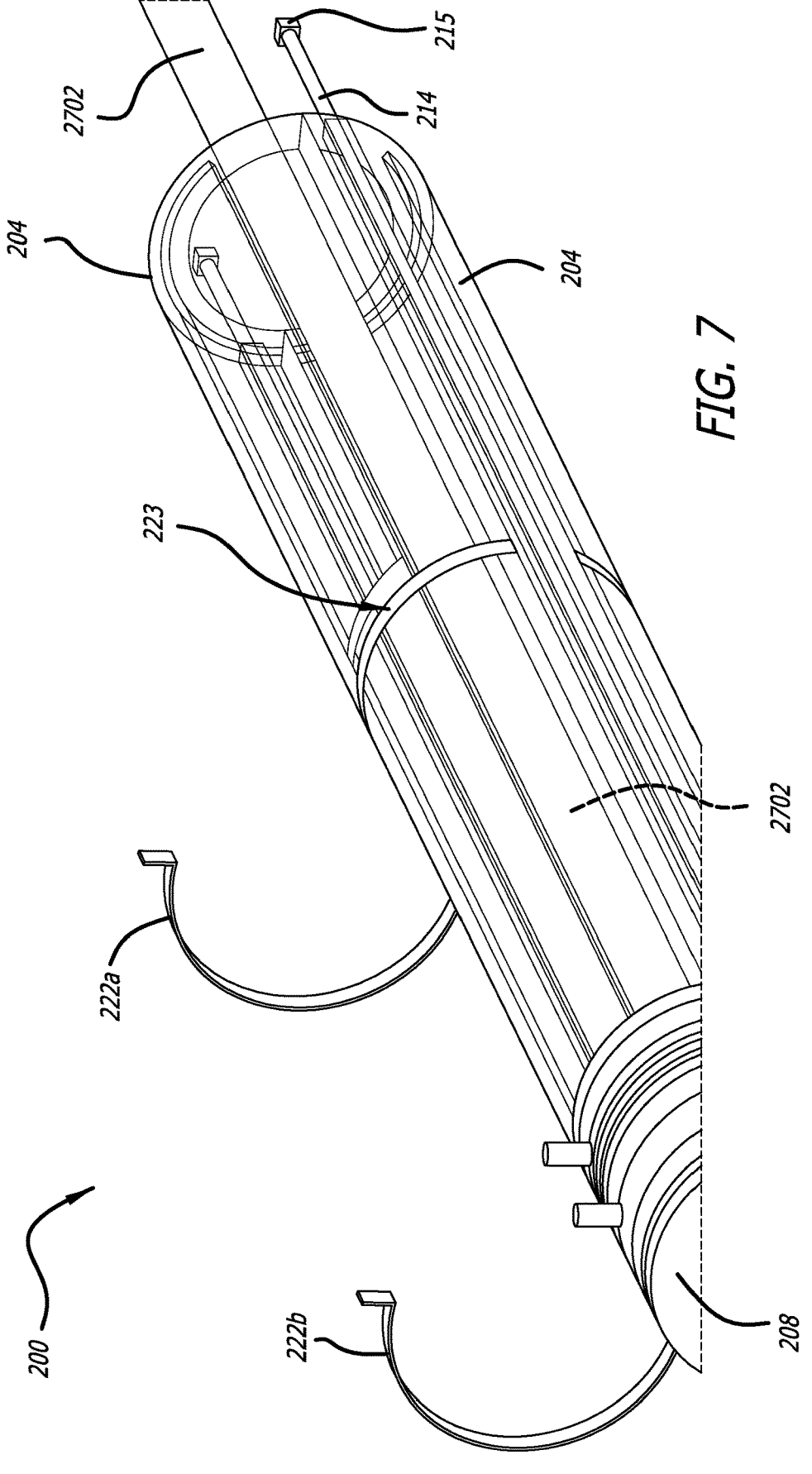
FIG. 7 illustrates first and second fasteners of the plurality of fasteners over the housing but unfastened from the fastening-side fastener rail in accordance with some embodiments.
Figure 8:
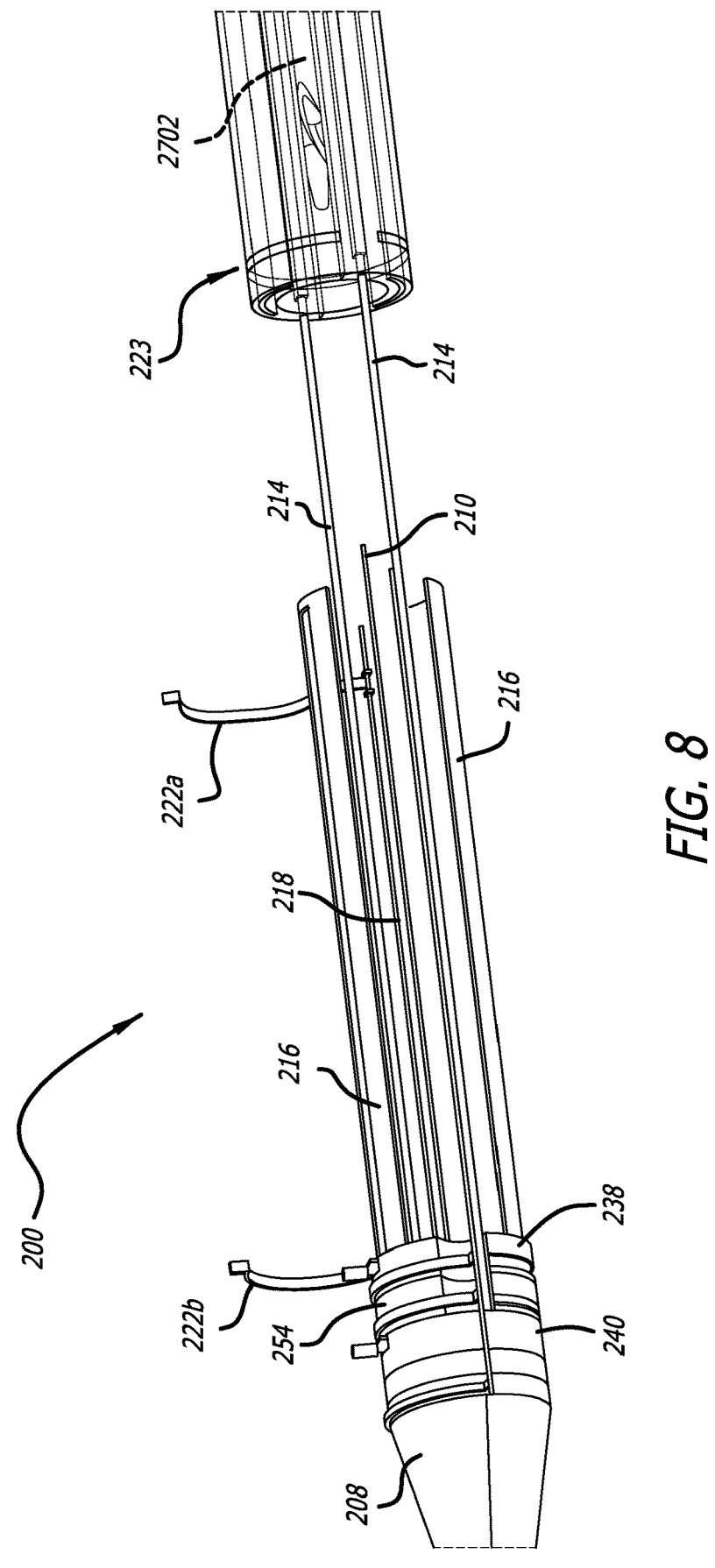
FIG. 8 illustrates the housing proximally withdrawn off top and bottom rails of the frame but remaining disposed over starboard-side and port-side rails in accordance with some embodiments.

Step 4: As shown in FIGS. 7 and 8, unfasten the fasteners 222*a* and 222*b*. Unfastening the fasteners 222*a* and 222*b* allows the housing 204 to be moved from its original position in the ready-to-deploy state of the access device 200.

Step 5: As further shown in FIG. 8, proximally withdraw the housing 204 with the catheter tube 2702 disposed therein off the top and bottom rails of the second pair of rails 216; however, keep the housing 204 disposed over the side rails of the first pair of rails 214.

Step 6: As shown FIGS. 11 and 12, unfasten the fastener 222*c*. Unfastening the fastener 222*c* allows the proximal guidewire clamp 238 of the access device 200 to be moved from its original position in the ready-to-deploy state of the access device 200.

Step 7: As further shown in FIG. 12, proximally withdraw the proximal guidewire clamp 238 along the second pair of rails 216 to a proximal portion thereof near the proximal end of the second pair of rails 216. Specifically, the proximal portion of the second pair of rails near the proximal end thereof should be under the fastener 222a.

Step 8: As shown in FIG. 13, clamp the access guidewire 210 in place in the proximal guidewire clamp 238 by pushing the moveable slide 248 farther into the groove 251 of the proximal guidewire clamp 238. Notably, as shown, the moveable slide 248 can include a push-pull tab atop the moveable slide 248 for clamping and opening the proximal guidewire clamp 238. When clamping the proximal guidewire clamp 238, the central through hole 246 between the movable slide 248 and the stationary slide 250 becomes smaller as the movable slide 248 is inserted farther into the groove 251 toward the stationary slide 250, thereby clamping the access guidewire 210 in place.

Step 9: As further shown in FIG. 13, fasten the fastener 222a, thereby keeping the proximal guidewire clamp 238 in place near the proximal end of the second pair of rails 216. When in place near the proximal end of the second pair of rails 216, the proximal guidewire clamp 238 provides a better hold on the access guidewire 210 for subsequently withdrawing the needle 206 from the access device 200 by the needle hub 254.

Figure 14:
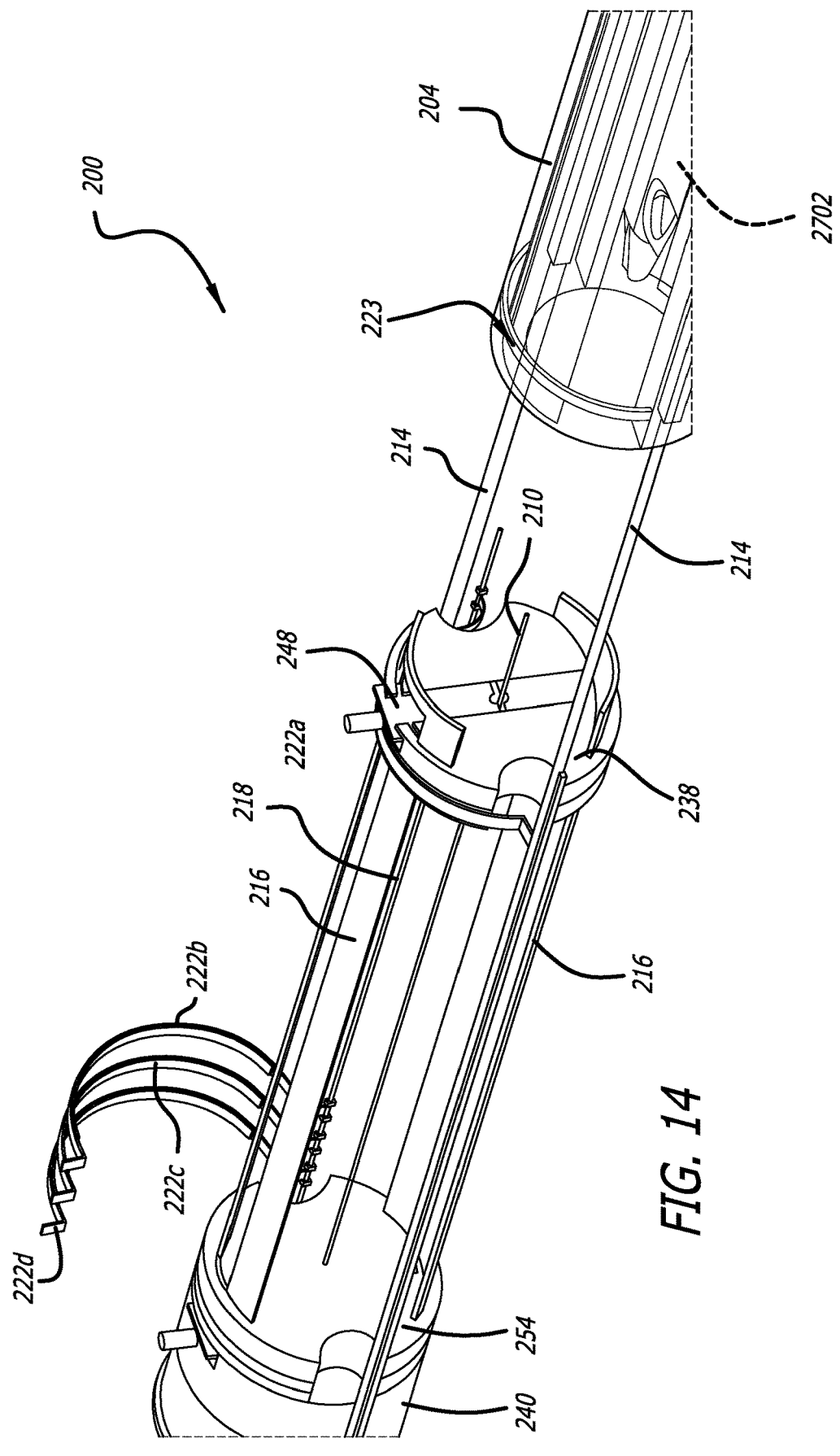
FIG. 14 illustrates a fourth fastener of the plurality of fasteners over the needle hub but unfastened from the fastening-side fastener rail in accordance with some embodiments.
Figure 15:
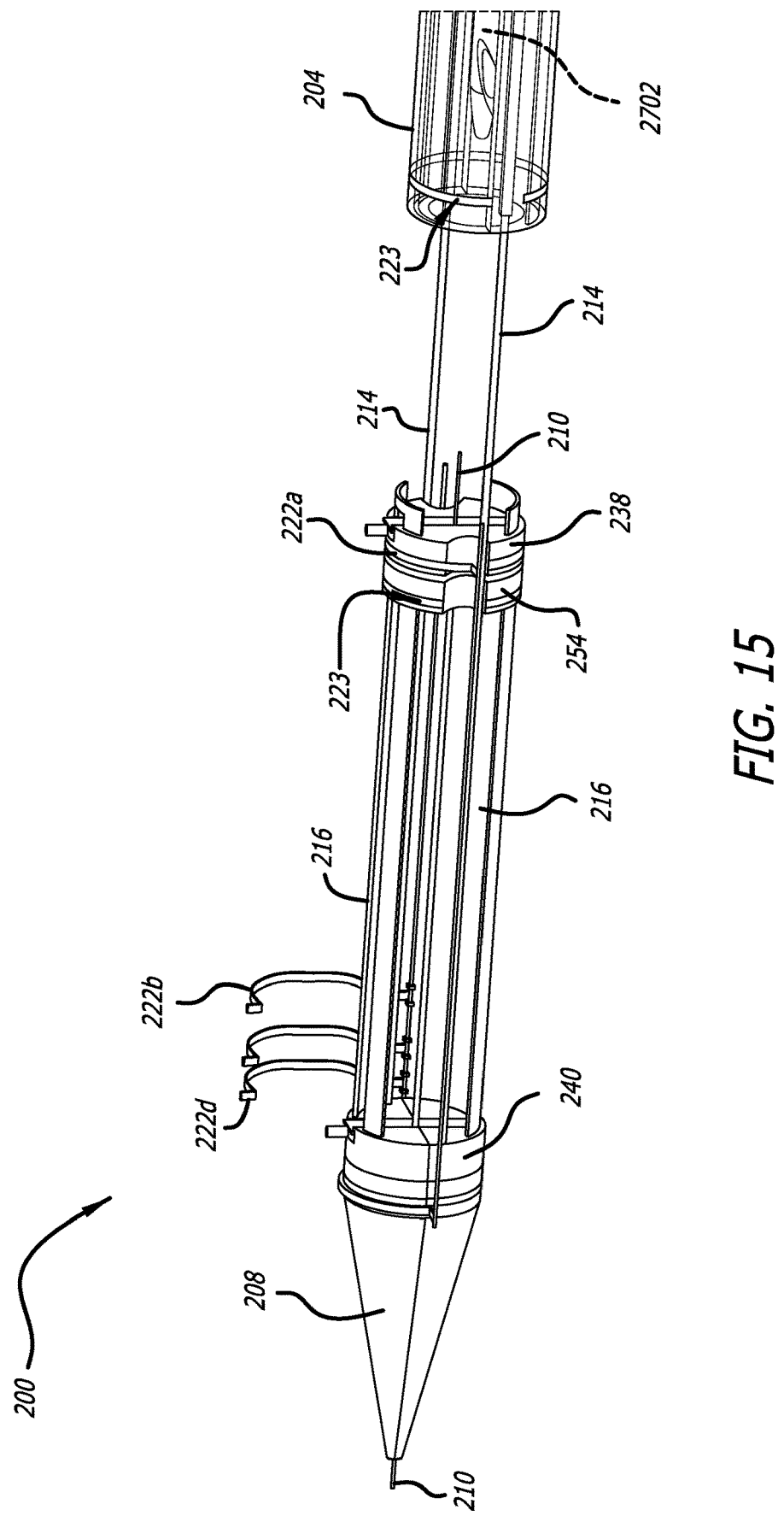
FIG. 15 illustrates the needle hub proximally withdrawn to the proximal guidewire clamp in accordance with some embodiments.
Figure 16:
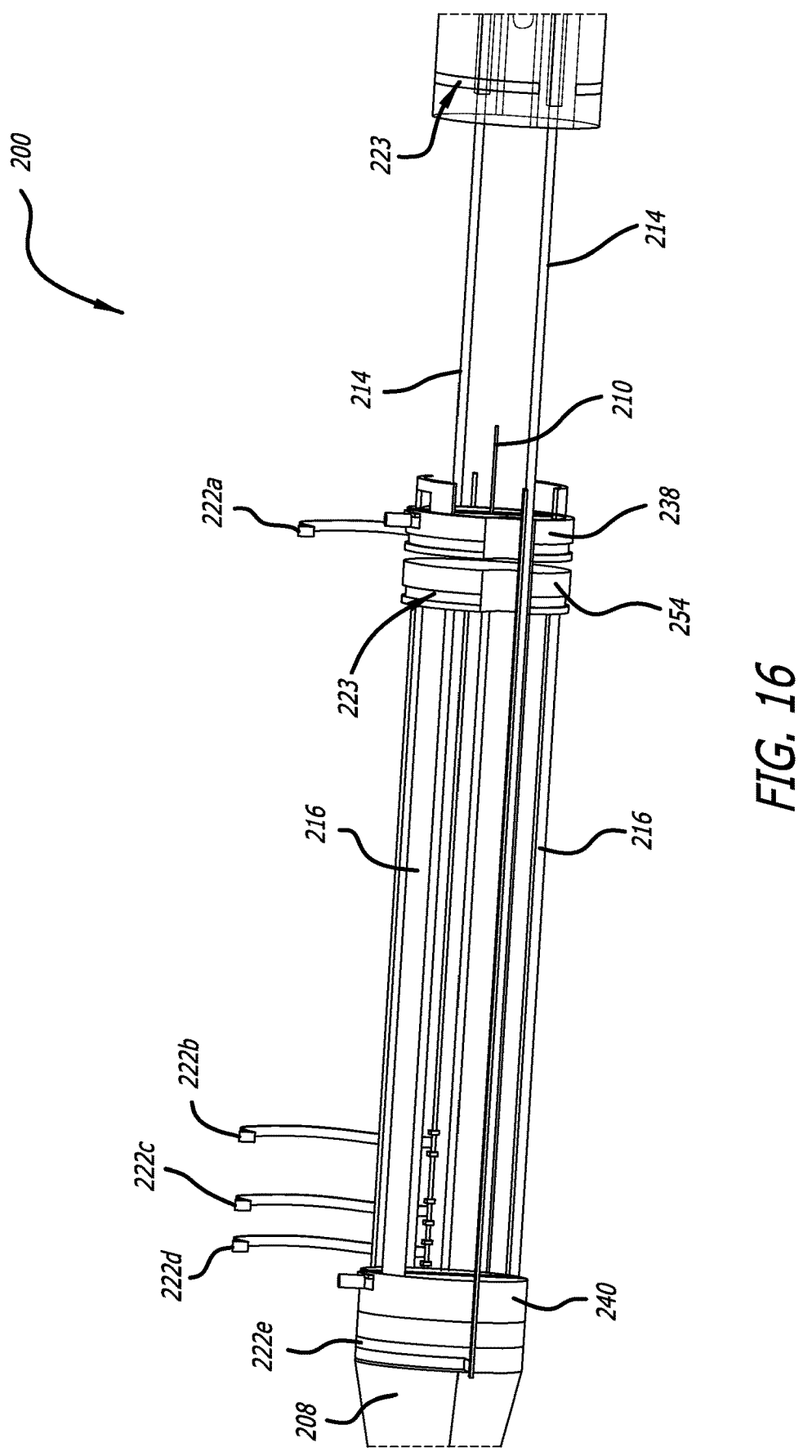
FIG. 16 illustrates the first fastener over the proximal guidewire clamp but unfastened from the fastening-side fastener rail in accordance with some embodiments.

Step 10: As shown in FIGS. 14-16, unfasten the fastener 222d. Unfastening the fastener 222d allows the needle hub 254 of the access device 200 to be moved from its original position in the ready-to-deploy state of the access device 200.

Step 11: As shown in FIG. 15, proximally withdraw the needle hub 254 along the second pair of rails 216 to the proximal guidewire clamp 238 fastened by the fastener 222a near the proximal end of the second pair of rails 216. When the needle hub 254 is in position next to the proximal guidewire clamp 238, the needle shaft 252 of the needle 206 is mostly if not entirely withdrawn from the components remaining in the distal end of the access device 200, for example, the distal guidewire clamp 240 and the dilator 208.

Step 12: As shown in FIG. 16, unfasten the fastener 222a. Unfastening the fastener 222a allows the proximal guidewire clamp 238 of the access device 200 to be subsequently removed from the access device 200.

Step 13: Open the proximal guidewire clamp 238 by withdrawing the moveable slide 248 from the groove 251 of the proximal guidewire clamp 238. Again, as shown, the moveable slide 248 can include the push-pull tab atop the moveable slide 248 for clamping and opening the proximal guidewire clamp 238. When opening the proximal guidewire clamp 238, the central through hole 246 between the movable slide 248 and the stationary slide 250 becomes larger as the movable slide 248 is withdrawn from the groove 251 away from the stationary slide 250, thereby releasing the access guidewire 210 from the proximal guidewire clamp 238.

Figure 17:
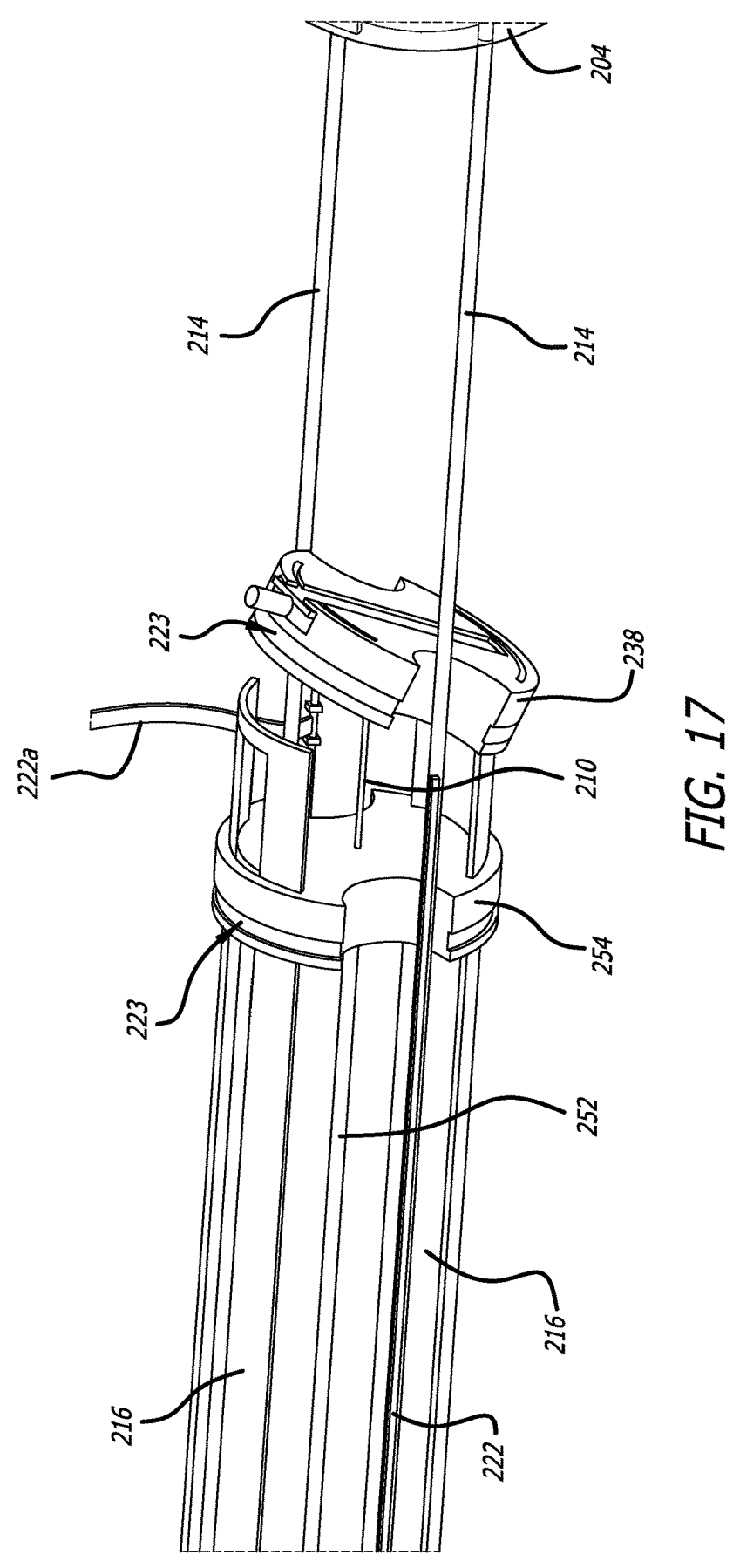
FIG. 17 illustrates removal of the proximal guidewire clamp from the access device in accordance with some embodiments.
Figure 18:
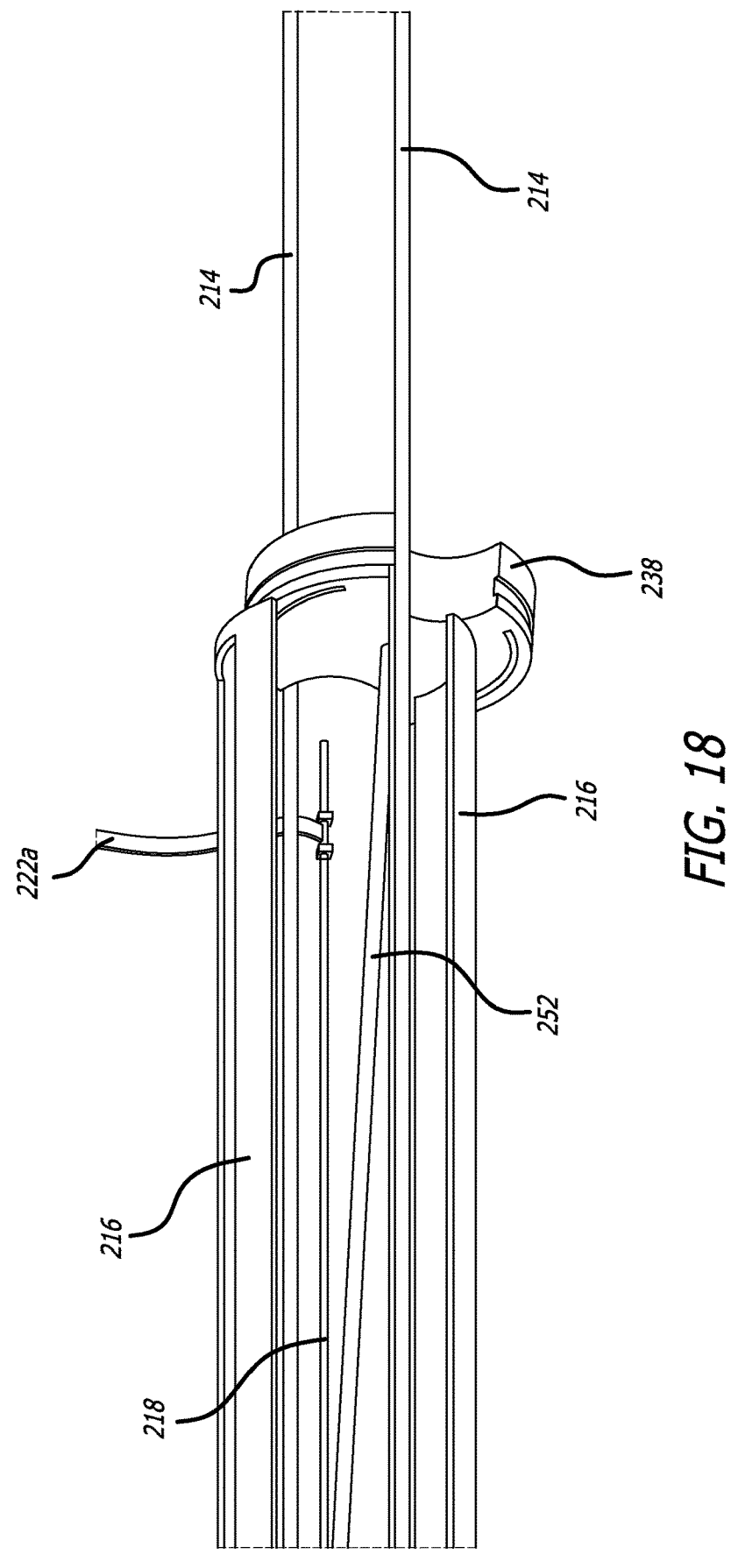
FIG. 18 illustrates removal of the needle from the access device in accordance with some embodiments.

Step 14: As shown in FIGS. 17 and 18, unload the proximal guidewire clamp 238 and the needle 206 from the access device 200 by completely withdrawing the proximal guidewire clamp 238 and the needle hub 254 proximally beyond the proximal end of the second pair of rails 216. Once the needle hub 254 is withdrawn beyond the proximal end of the second pair of rails 216, the needle shaft 252 of the needle 206 is entirely withdrawn from the dilator 208. Once the needle tip 253 is withdrawn beyond the proximal end of the second pair of rails 216, the needle 206 is mostly if not entirely withdrawn from over the access guidewire 210.

Figure 19:
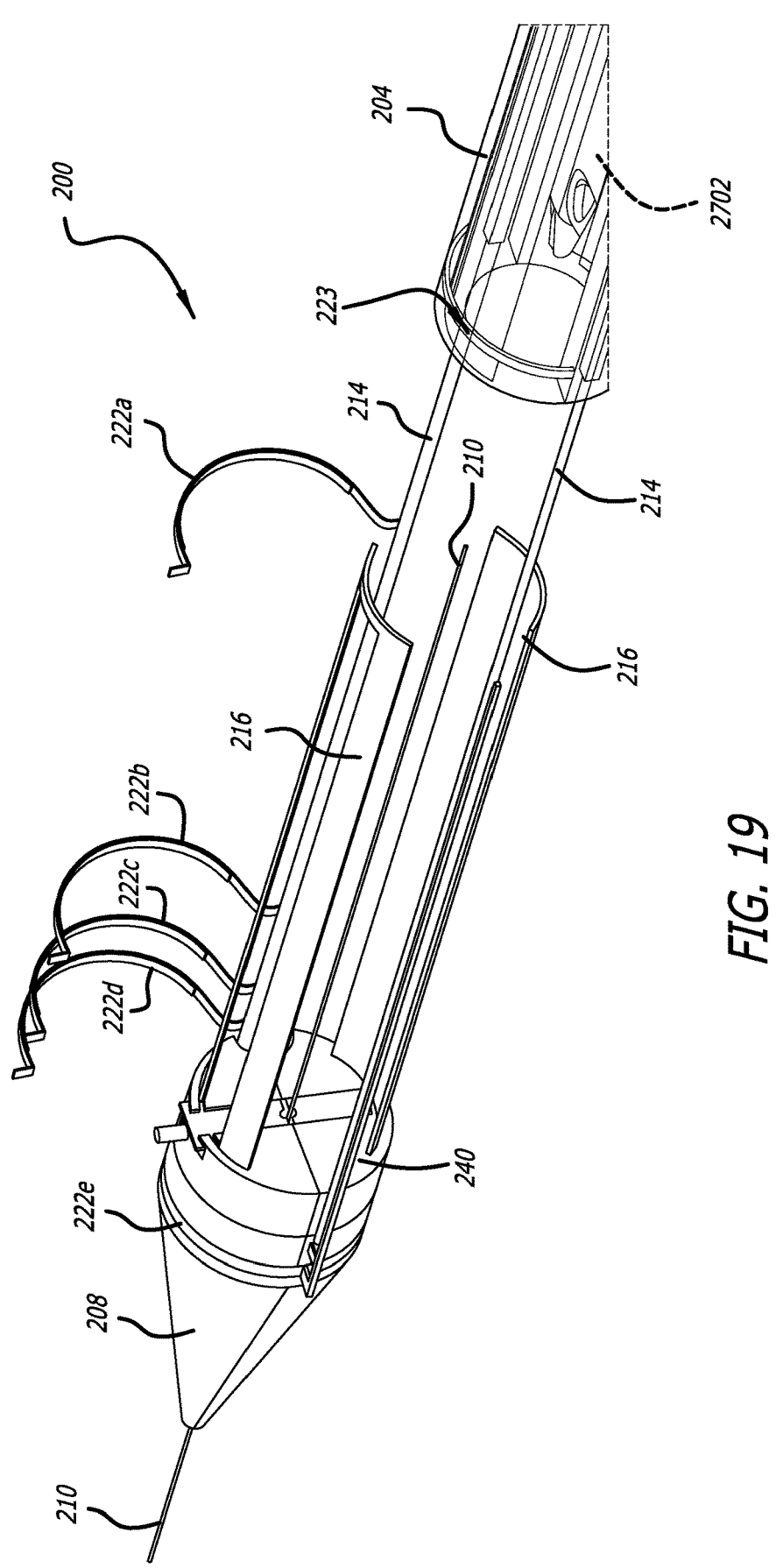
FIG. 19 illustrates a distal guidewire clamp adjacent an end portion of the frame as in the ready-to-deploy state of the access device in accordance with some embodiments.
Figure 20:
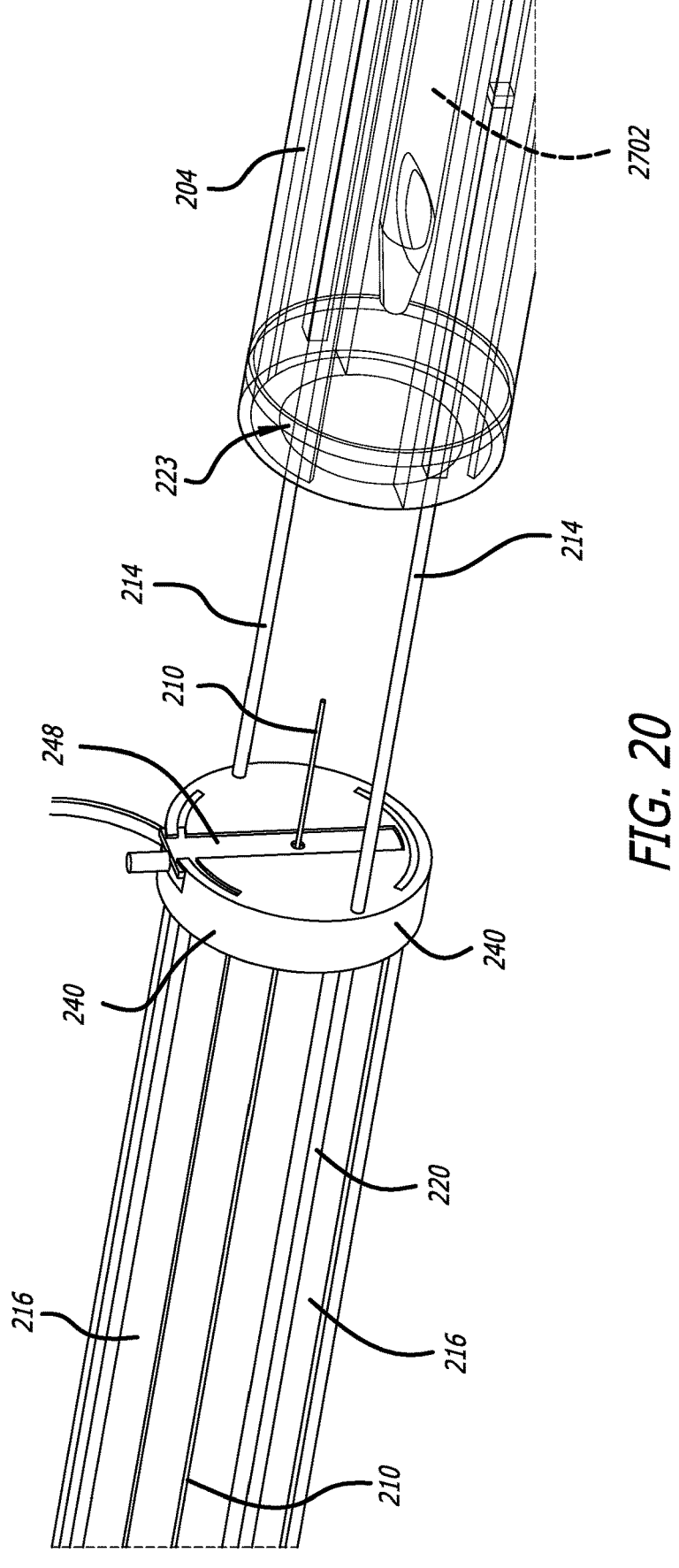
FIG. 20 illustrates the distal guidewire clamp proximally withdrawn to a proximal end of the top and bottom rails of the frame and the access guidewire clamped by the distal guidewire clamp in accordance with some embodiments.

Step 15: Proximally withdraw the distal guidewire clamp 240 along the second pair of rails 216 to the proximal end of the second pair of rails 216 but not beyond the proximal end of the second pair of rails 216. FIG. 19 shows the distal guidewire clamp 240 coupled to or at least abutting the end portion 212 of the frame 202 as in the ready-to-deploy state of the access device 200, whereas FIG. 20 shows the distal guidewire clamp 240 withdrawn to the proximal end of the second pair of rails 216.

Step 16: As shown in FIG. 20, clamp the access guidewire 210 in place in the distal guidewire clamp 240 by pushing the moveable slide 248 farther into the groove 251 of the distal guidewire clamp 240. Notably, as shown, the moveable slide 248 can include a push-pull tab atop the moveable slide 248 for clamping and opening the distal guidewire clamp 240. When clamping the proximal guidewire clamp 238, the central through hole 246 between the movable slide 248 and the stationary slide 250 becomes smaller as the movable slide 248 is inserted farther into the groove 251 toward the stationary slide 250, thereby clamping the access guidewire 210 in place.

Step 17: As shown between FIGS. 20 and 21, distally advance the housing 204 with the catheter tube 2702 disposed therein along the first pair of rails 214 to the distal guidewire clamp 240 and, in the same motion, thread a distal lumen of the catheter 2700 over a proximal end of the access guidewire 210 that extends beyond the distal guidewire clamp 240.

Figure 21:
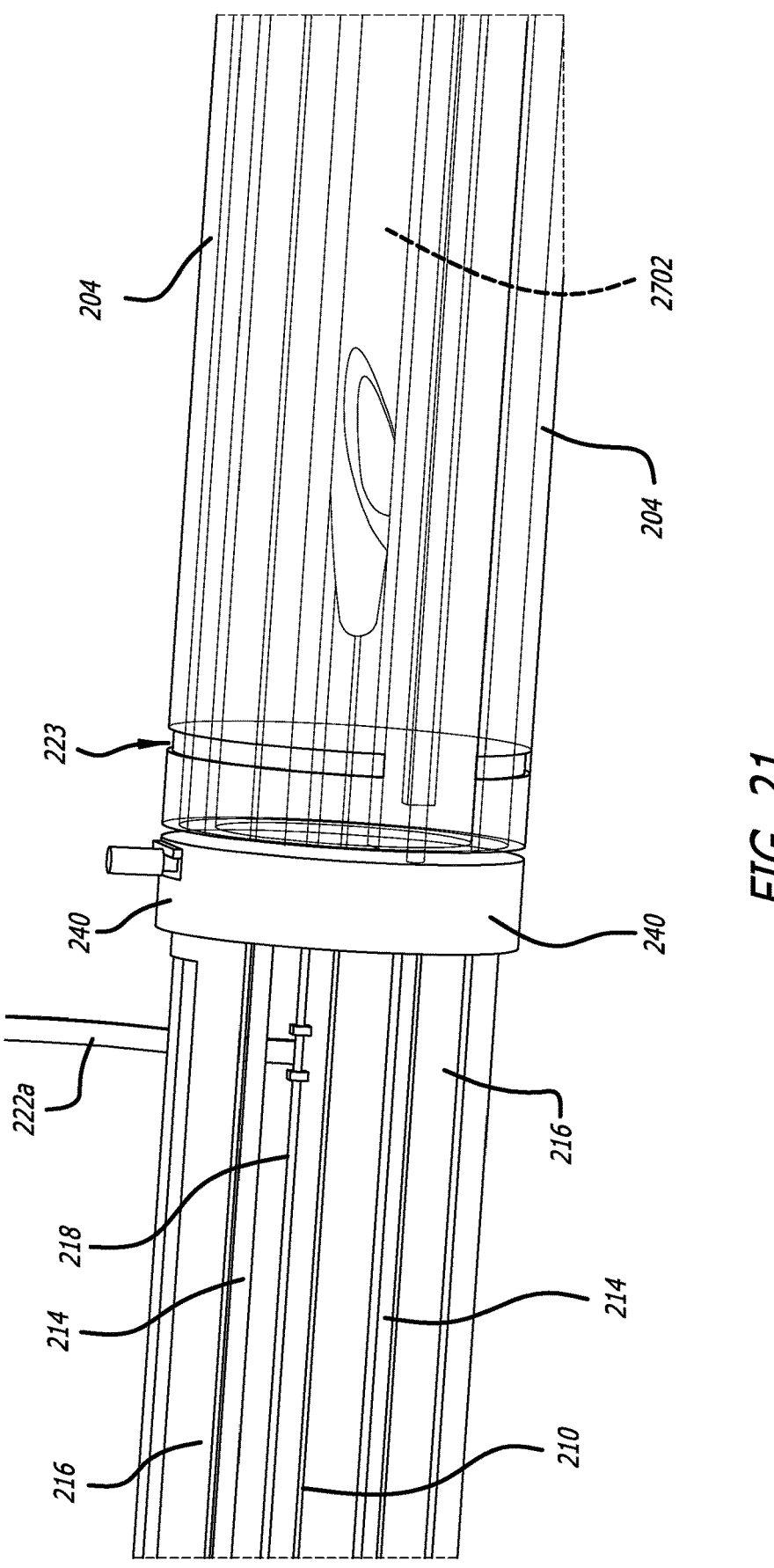
FIG. 21 illustrates the housing distally advanced to the distal guidewire clamp at the proximal end of the top and bottom rails of the frame and the catheter threaded over a proximal end of the access guidewire in accordance with some embodiments.

Step 18: As shown in FIG. 21, open the distal guidewire clamp 240 by withdrawing the moveable slide 248 from the groove 251 of the distal guidewire clamp 240. Again, as shown, the moveable slide 248 can include the push-pull tab atop the moveable slide 248 for clamping and opening the distal guidewire clamp 240. When opening the distal guidewire clamp 240, the central through hole 246 between the movable slide 248 and the stationary slide 250 becomes larger as the movable slide 248 is withdrawn from the groove 251 away from the stationary slide 250, thereby releasing the access guidewire 210 from the distal guidewire clamp 240.

Figure 22:
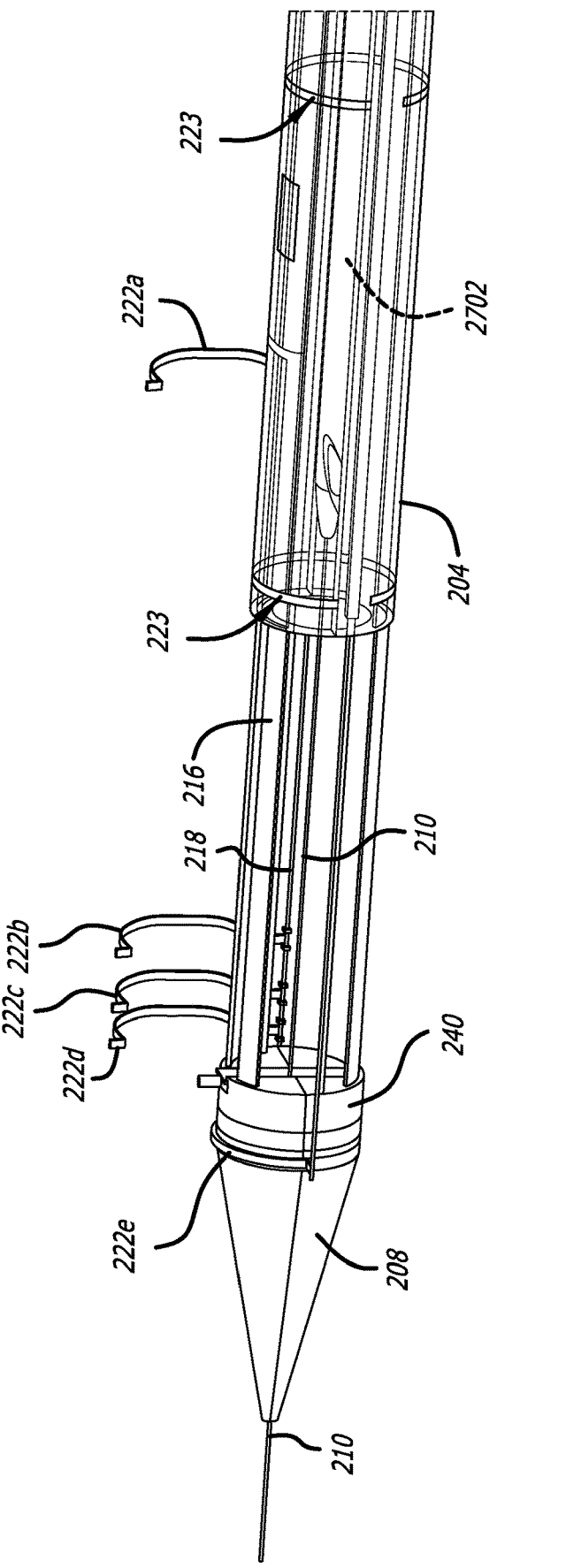
FIG. 22 illustrates the distal guidewire clamp distally advanced to the end portion of the frame and the catheter further threaded over the access guidewire in accordance with some embodiments.
Figure 23:
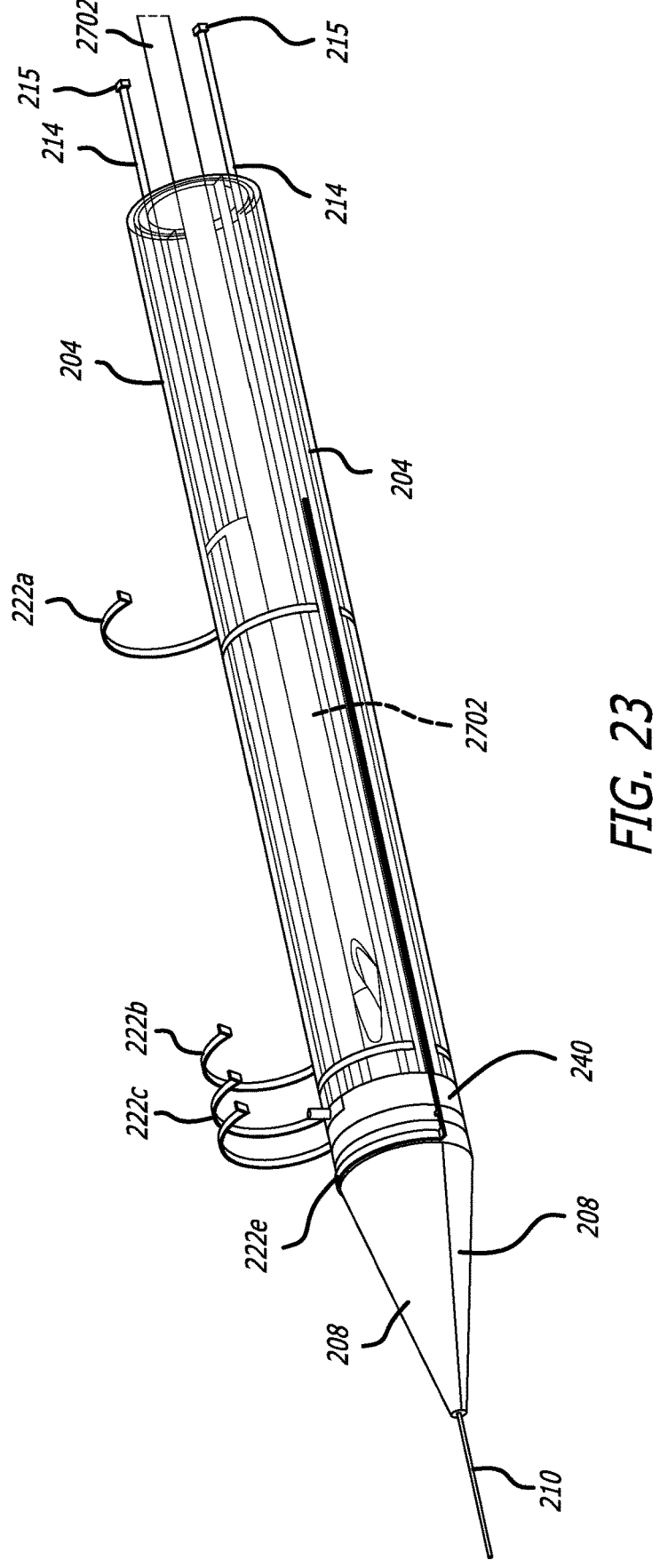
FIG. 23 illustrates the housing advanced to the distal guidewire clamp at the end portion of the frame and the catheter fully threaded over the access guidewire in accordance with some embodiments.

Step 19: Distally advance the distal guidewire clamp 240 and the housing 204 with the catheter tube 2702 disposed therein, separately or together, beginning with the distal guidewire clamp 240, along the second pair of rails 216 until abutting the end portion 212 of the frame 202. FIG. 21 to FIG. 22 shows advancement of the distal guidewire clamp 240 while FIG. 22 to FIG. 23 shows advancement of the housing 204 with the catheter tube 2702 disposed therein separately.

Figure 24:
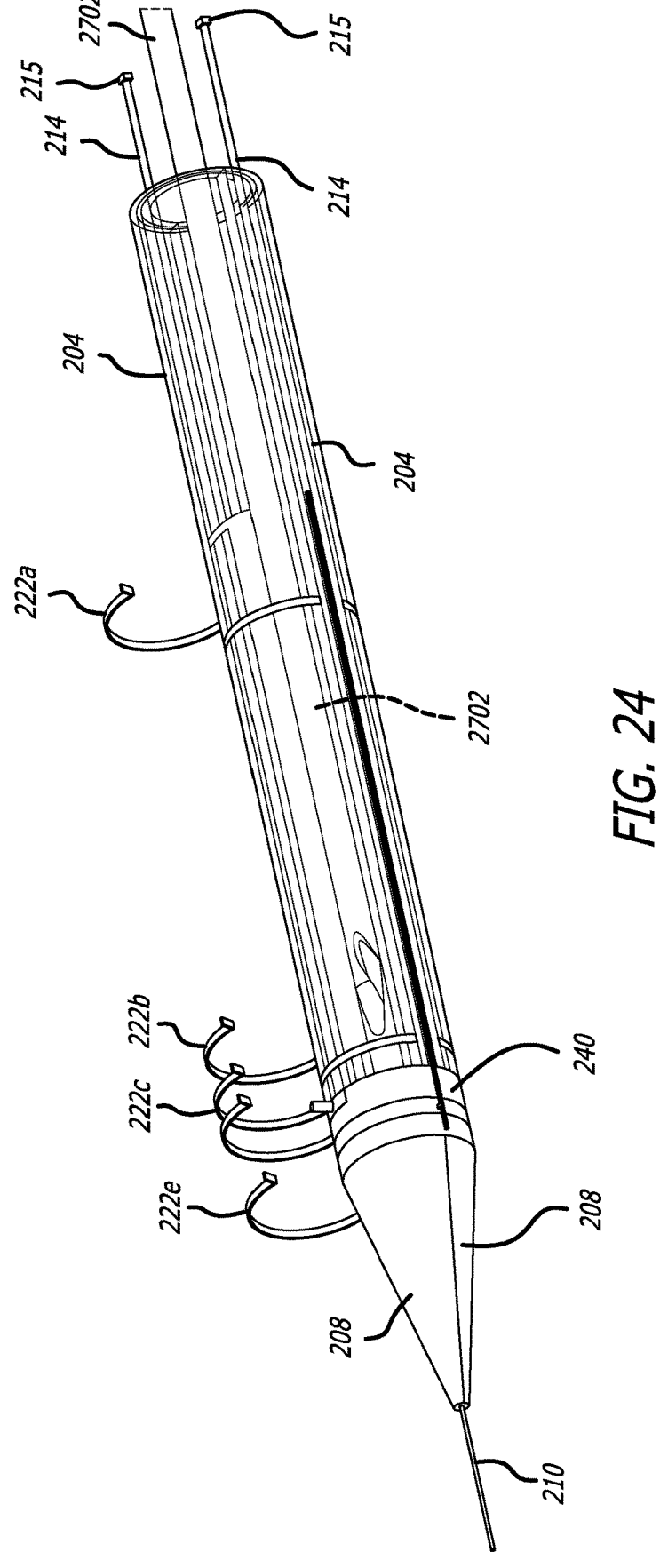
FIG. 24 illustrates a fifth fastener of the plurality of fasteners over a dilator but unfastened from the fastening-side fastener rail in accordance with some embodiments.

Step 20: As shown in FIG. 24, unfasten the fastener 222e. Unfastening the fastener 222e allows the dilator 208 of the access device 200 to be moved from its original position in the ready-to-deploy state of the access device 200. Unfastening the fastener 222e also allows the dilator 208 to be split along its length for subsequent removal from the access guidewire 210.

Figure 25:
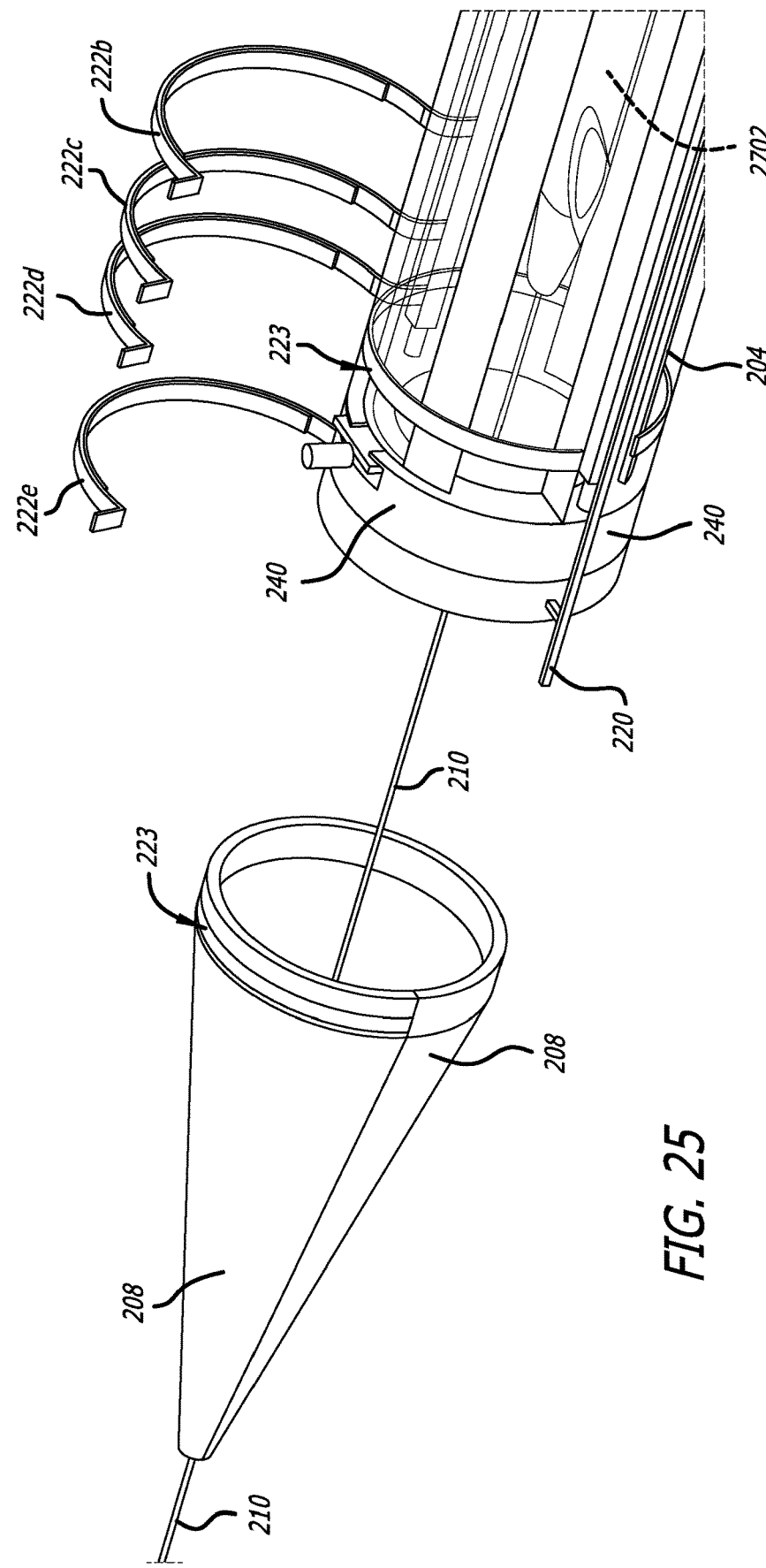
FIG. 25 illustrates the dilator distally advanced over the access guidewire for dilation of an insertion site in a body of a patient in accordance with some embodiments.

Step 21: As shown in FIG. 25, distally advance the dilator 208 from the end portion 212 of the frame 202, thereby separating the dilator 208 from the access device 200.

Step 22: Dilate the insertion site of the patient with the dilator 208 by following the access guidewire 210 with the dilator 208 to the insertion site and dilating the insertion site, thereby establishing a dilated insertion site.

Step 23: Withdraw the dilator 208 from the dilated insertion site.

Figure 26:
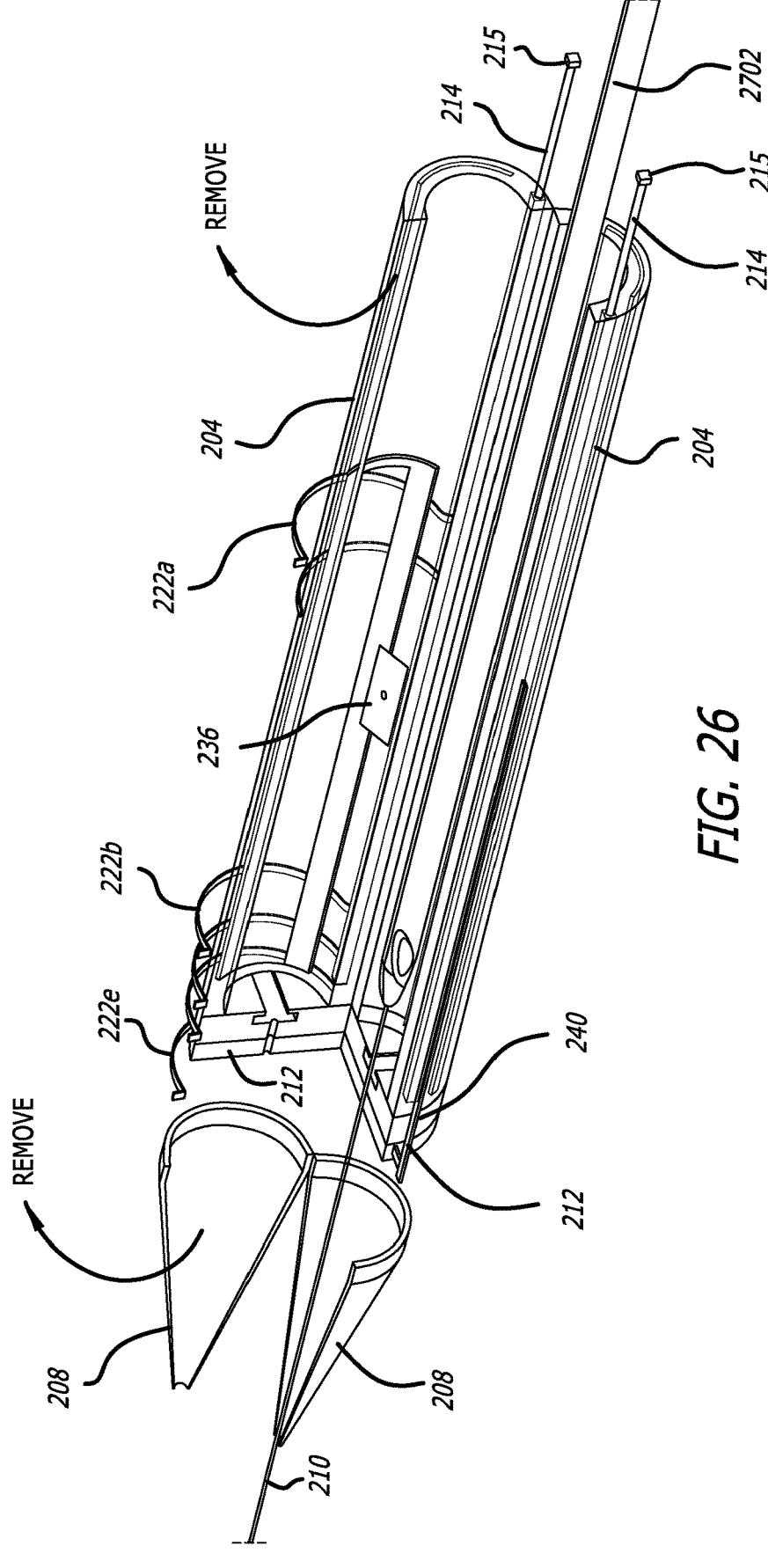
FIG. 26 illustrates the housing, the frame, the distal guidewire clamp, and the dilator split along their lengths for removal of the access device from around the access guidewire and the catheter after the dilation in accordance with some embodiments.
Figure 27:
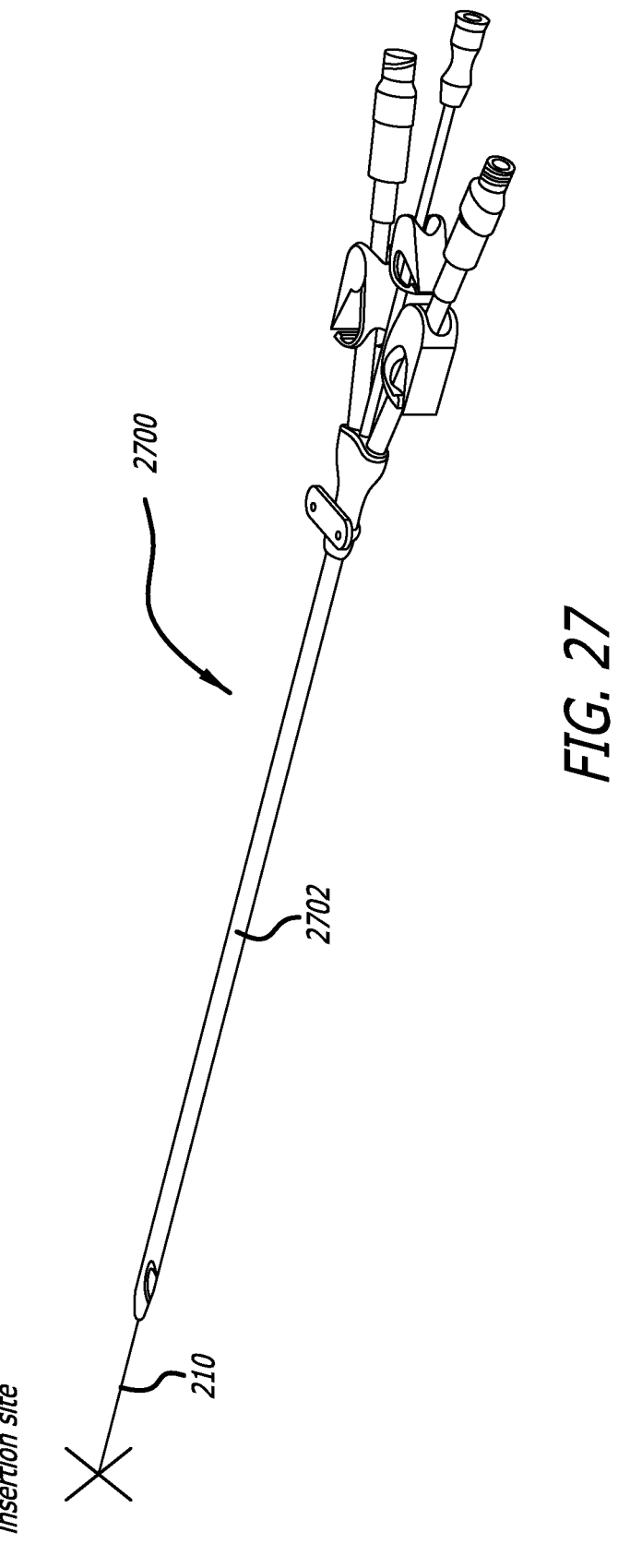
FIG. 27 illustrates the catheter over the access guidewire after removal of the access device from around the access guidewire and the catheter in accordance with some embodiments.
Figure 28:
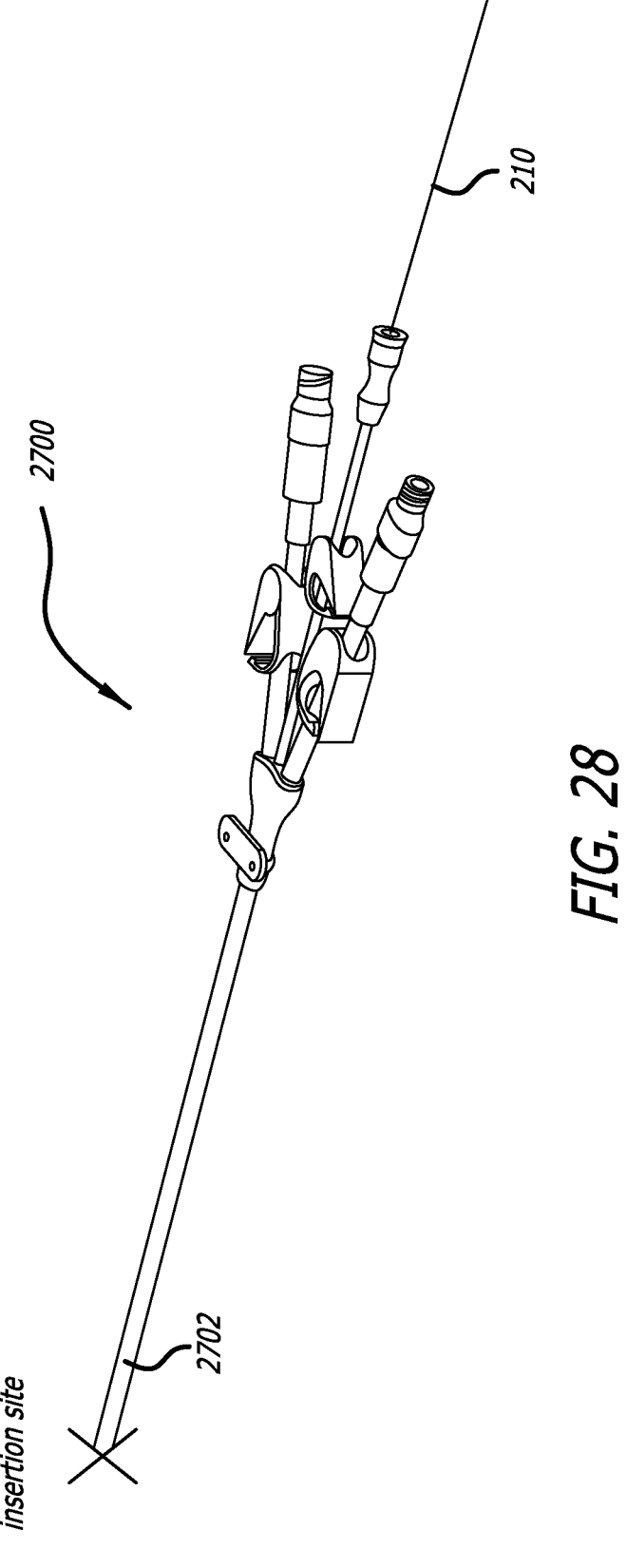
FIG. 28 illustrates the catheter inserted into the insertion site in accordance with some embodiments.

Step 24: As shown in FIGS. 26 and 27, remove by the dilator 208 from around the access guidewire 210 by separating the top and bottom portions of the dilator 208 and withdrawing the top and bottom portions of the dilator 208 from the access guidewire 210.

Step 25: As further shown between FIGS. 26 and 27, remove a remainder of the access device 200 (e.g., the frame 202, the distal guidewire holder 240, and the housing 204) from around the access guidewire 210 by separating the top and bottom portions of the remainder of the access device (e.g., the top and bottom portions of the frame 202, the top and bottom portions of the distal guidewire holder 240, and the top and bottom portions of the housing 204) and withdrawing the top and bottom portions of the access device 200 from the access guidewire 210.

Step 26. Insert the catheter over the access guidewire 210.

Step 27. Withdraw the access guidewire 210 from the patient.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An access device for internal access to a body of a patient, comprising:
   a longitudinal frame including a distal end portion;
   a longitudinal housing disposed on the longitudinal frame;
   a pair of guidewire clamps disposed on the longitudinal frame between the distal end portion of the longitudinal frame and a distal end of the longitudinal housing in a ready-to-deploy state of the access device, each guidewire clamp of the pair of guidewire clamps configured to clamp an access guidewire disposed in the access device;
   a needle including a needle shaft coupled to a needle hub, the needle hub disposed on the longitudinal frame between the pair of guidewire clamps; and
   a dilator distally extending from the distal end portion of frame to which the dilator is coupled in the ready-to-deploy state of the access device, the needle shaft distally extending beyond a distal end of the dilator in the ready-to-deploy state of the access device, thereby allowing the needle to establish an insertion site for the internal access to the body of the patient.

2. The access device of claim 1, wherein the frame includes a plurality of rails proximally extending from the distal end portion, and wherein the longitudinal housing includes a pair of housing channels configured to slidably accept therein a first pair of rails of the plurality of rails, and the needle hub includes at least a pair of needle-hub peripheral through holes configured to slidably accept therein a second pair of rails of the plurality of rails.

3. The access device of claim 2, wherein at least one guidewire clamp of the pair of guidewire clamps includes a pair of guidewire-clamp peripheral through holes configured to slidably accept therein the second pair of rails.

4. The access device of claim 2, wherein the needle hub and at least one guidewire clamp of the pair of guidewire clamps includes a pair of cutouts configured to bypass the first pair of rails.

5. The access device of claim 2, wherein the first pair of rails and the second pair of rails are orthogonal to each other.

6. The access device of claim 2, wherein the first pair of rails is longer than the second pair of rails, thereby allowing the longitudinal housing to slide beyond a proximal end of the second pair of rails for removal of at least the needle from the access device.

7. The access device of claim 1, wherein the longitudinal housing is configured to accept therein a catheter tube, the longitudinal housing configured to maintain sterility of the catheter tube during a procedure for placing the catheter tube in the body of the patient with the access device after dilation of the insertion site with the dilator.

8. The access device of claim 7, wherein the longitudinal housing is transparent, thereby allowing the catheter tube to be viewed while distally advancing the longitudinal housing over the frame and simultaneously threading the catheter tube over a proximal end of the access guidewire.

9. The access device of claim 1, wherein the longitudinal housing includes a sidewall guidewire clamp disposed in a sidewall of the longitudinal housing, the sidewall guidewire clamp configured to i) clamp and hold the access guidewire in position in the needle shaft while establishing the insertion site with the needle and ii) open and allow the access guidewire to be distally advanced into the body of the patient through the insertion site.

10. The access device of claim 1, wherein each guidewire clamp of the pair of guidewire clamps includes a captive but movable slide configured to slide into a groove of each guidewire clamp and clamp the access guidewire when the access guidewire is threaded through a central through hole in each guidewire clamp.

11. The access device of claim 10, wherein each guidewire clamp of the pair of guidewire clamps includes a stationary slide disposed in the groove of each guidewire clamp on an opposite side of the central through hole from the captive but moveable slide, the stationary slide configured to oppose the captive but movable slide when clamping the access guidewire.

12. The access device of claim 1, wherein the pair of guidewire clamps includes a proximal guidewire clamp and a distal guidewire clamp.

13. The access device of claim 12, wherein the distal guidewire clamp proximally extends from the distal end portion of the frame to which the distal guidewire clamp is coupled in the ready-to-deploy state of the access device.

14. The access device of claim 12, wherein the frame, the longitudinal housing, the dilator, and the distal guidewire clamp are configured to split along their lengths for removal from around at least the access guidewire when the access guidewire is disposed in the body of the patient through the insertion site.

15. The access device of claim 1, further comprising a plurality of fasteners configured to fasten components of the access device together and keep the components in position in the ready-to-deploy state of the access device, the components including at least the longitudinal housing, at least one guidewire clamp of the pair of guidewire clamps, the needle hub, and the dilator.

16. The access device of claim 15, wherein each fastener of the plurality of fasteners is irremovably coupled by a hinge to a hinged-side fastener rail and removably fastened to a fastening-side fastener rail in the ready-to-deploy state of the access device.

17. The access device of claim 15, wherein at least one fastener of the plurality of fasteners is configured to double for fastening the longitudinal housing in the ready-to-deploy state of the access device and at least one guidewire clamp of the pair of guidewire clamps for clamping the access guidewire while proximally withdrawing the needle from the insertion site.

18. An access system for internal access to a body of a patient, comprising:

a catheter; and an access device including:

a longitudinal frame including a distal end portion;

a longitudinal housing disposed on the longitudinal frame, a catheter tube of the catheter disposed in the longitudinal housing a ready-to-deploy state of the access system;

a pair of guidewire clamps disposed on the longitudinal frame between the distal end portion of the longitudinal frame and a distal end of the longitudinal housing in the ready-to-deploy state of the access system, each guidewire clamp of the pair of guidewire clamps configured to clamp an access guidewire disposed in the access device;

a needle including a needle shaft coupled to a needle hub, the needle hub disposed on the longitudinal frame between the pair of guidewire clamps; and a dilator distally extending from the distal end portion of frame to which the dilator is coupled in the ready-to-deploy state of the access system, the needle shaft distally extending beyond a distal end of the dilator in the ready-to-deploy state of the access system, thereby allowing the needle to establish an insertion site for the internal access to the body of the patient.

19. The access system of claim 18, wherein the catheter is an acute dialysis catheter and the internal access to the body of the patient is vascular access by way of a jugular, a subclavian, or a femoral vein of the patient.

* * * * *